US008859742B2

(12) United States Patent
Li et al.

(10) Patent No.: US 8,859,742 B2
(45) Date of Patent: Oct. 14, 2014

(54) DIAGNOSTIC ASSAYS FOR CHORDOPOXVIRUSES

(75) Inventors: Yu Li, Duluth, GA (US); Inger K. Damon, Decatur, GA (US); Hui Zhao, Lilburn, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 0 days.

(21) Appl. No.: 13/505,719

(22) PCT Filed: Nov. 2, 2010

(86) PCT No.: PCT/US2010/055061
§ 371 (c)(1),
(2), (4) Date: May 2, 2012

(87) PCT Pub. No.: WO2011/056771
PCT Pub. Date: May 12, 2011

(65) Prior Publication Data
US 2012/0214155 A1    Aug. 23, 2012

Related U.S. Application Data

(60) Provisional application No. 61/257,582, filed on Nov. 3, 2009.

(51) Int. Cl.
*C12Q 1/68*    (2006.01)
*C12Q 1/70*    (2006.01)

(52) U.S. Cl.
CPC ..................................... *C12Q 1/701* (2013.01)
USPC ............................ 536/6.1; 435/6.12; 536/23.1

(58) Field of Classification Search
None
See application file for complete search history.

(56) References Cited

U.S. PATENT DOCUMENTS

| | | | |
|---|---|---|---|
| 5,629,179 A * | 5/1997 | Mierendorf et al. | 435/91.2 |
| 7,645,456 B2 * | 1/2010 | Weltzin et al. | 424/232.1 |
| 2005/0025747 A1 * | 2/2005 | Laidlaw et al. | 424/93.2 |
| 2006/0057600 A1 | 3/2006 | Duerksen-Hughes et al. | |
| 2006/0147905 A1 | 7/2006 | Mirzabekov et al. | |
| 2007/0054263 A1 | 3/2007 | Czub et al. | |
| 2009/0081675 A1 | 3/2009 | Colston | |
| 2009/0155244 A1 | 6/2009 | Roper | |

FOREIGN PATENT DOCUMENTS

| EP | 1709971 A1 | 10/2006 |
|---|---|---|
| WO | WO 2004/092420 A1 | 10/2004 |
| WO | WO 2007130519 A2 * | 11/2007 |

OTHER PUBLICATIONS

Sonntag et al. (Identification and properties of the genes encoding the poly(A) polymerase and a small (22 kDa) and the largest subunit (147 kDa) of the DNA-dependent RNA polymerase of molluscum contagiosum virus, Virology. Jul. 10, 1995;210(2):471-8; as evidenced by NCBI Accesion No. L38927).*
Tulman et al. (The Genome of Canarypox Virus, Journal of Virology, Jan. 2004, p. 353-366; as evidenced by NCBI Accesion No. AY318871).*
Lee et al. (The Genome Sequence of Yaba-like Disease Virus, a Yatapoxvirus, Virology 281, 170±192 (2001); as evidenced by NCBI Accesion No. AJ293568).*
NCBI Accession No. X76267 (2005).*
Rozen et al. (Primer3 on the WWW for General Users and for Biologist Programmers, in Methods in Molecular Biology, vol. 132: Bioinformatics Methods and Protocols, 2000).*
Buck et al. ("Design Strategies and Performance of Custom DNA Sequencing Primers" Biotechniques. 1999. 27(3): pp. 528-536).*
Lowe et al. (Nucleic Acids Research, vol. 18, No. 7, p. 1757-1761, 1990).*
Ju et al. (Design and Synthesis of Fluorescence Energy Transfer Dye-Labeled Primers and Their Application for DNA Sequencing and Analysis, Analytical Biochem., 231;131-140 (1995)).*
Weiner et al. (Kits and their unique role in molecular biology: a brief retrospective, BioTechniques 44:701-704 (25th Anniversary Issue, Apr. 2008)).*
Stratagene ("Gene Characterization Kits" 1988).*
Bekaert et al. (UniPrime: a workflow-based platform for improved universal primer design, Nucleic Acids Research, Apr. 19, 2008, vol. 36, No. 10).*
Boutros et al. (UniPrime2: a web service providing easier Universal Primer design, Nucleic Acids Research, Apr. 28, 2009, vol. 37).*
Zhang et al. (Universal primers for HBV genome DNA amplification across subtypes: a case study for designing more effective viral primers, Virology Journal, Sep. 24, 2007, 4:92).*
Li et al., "GC Content-Based Pan-Pox Universal PCR Assays for Poxvirus Detection," *J. Clin. Microbiol.*, 48(1):268-276, 2009.
Heine et al., "A capripoxvirus detection PCR and antibody ELISA based on the major antigen P32, the homolog of the vaccinia virus H3L gene," *J Immunol Meth*, 227(1-2):187-196, 1999 (Abstract only).
Kulesh et al., "Monkeypox virus detection in rodents using real-time 3'-minor groove binder TaqMan assays on the Roche LightCycler," *Lab Invest*, 84:1200-1208, 2004.

(Continued)

*Primary Examiner* — Christopher M Babic
*Assistant Examiner* — Aaron Priest
(74) *Attorney, Agent, or Firm* — Klarquist Sparkman, LLP

(57) ABSTRACT

This disclosure relates to compositions and methods of their use in detection and identification of a chordopoxvirus in a sample, such as diagnosis of an infection in a subject. The compositions and methods allow for detection and identification of all non-avian low-GC content chordopoxviruses, identification of most known high-GC content chordopoxvirus, and species-specific detection of Canarypox virus, Fowlpox virus, and Sealpox virus.

15 Claims, 6 Drawing Sheets

(56) References Cited

OTHER PUBLICATIONS

Mangana-Vougiouka et al., "Sheep poxvirus identification from clinical specimens by PCR, cell culture, immunofluorescence and agar gel immunoprecipitation assay," *Mol Cell Probes*, 14(5):305-310, 2000 (Abstract only).

Neubauer et al., "Specific detection of monkeypox virus by polymerase chain reaction," *J Virol Meth*, 74(2):201-207, 1998 (Abstract only).

Nitsche et al., "Detection of Orthopoxvirus DNA by Real-Time PCR and Identification of Variola Virus DNA by Melting Analysis," *J Clin Micro*, 42(3):1207-1213, 2004.

Nitsche et al., "Detection of Infectious Poxvirus Particles," *Emerg Infect Dis*, 12(7):1139-1141, 2006.

Fedele et al., "Use of Internally Controlled Real-Time Genome Amplification for Detection of Variola Virus and Other Orthopoxviruses Infecting Humans," *Journal of Clinical Microbiology*, 44(12):4464-4470, 2006.

Lapa et al., "Species-Level Identification of Orthopoxviruses with an Oligonucleotide Microchip," *Journal of Clinical Microbiology*, 40(3): 753-757, 2002.

Laassri et al, "Detection and discrimination of orthopoxviruses using microarrays of immobilized oligonucleotides," *Journal of Virological Methods*, 112(1-2): 67-78, 2003.

Li et al, "GC Content-Based Pan-Pox Universal PCR Assays for Poxvirus Detection," *Journal of Clinical Microbiology, American Society for Microbiology*, 48(1): 268-276, 2010.

Loparev et al., "Detection and differentiation of old world orthopoxviruses: restriction fragment length polymorphism of the crmB gene region," *Journal of Clinical Microbiology, American Society for Microbiology*, 39(1): 94-100, 2001.

Meyer et al., "Gene for A-type inclusion body protein is useful for a polymerase chain reaction assay to differentiate orthopoxviruses," *Journal of Virological Methods*, 64(2): 217-221, 1997.

Olson et al., "Real-Time PCR System for Detection of Orthopoxviruses and Simultaneous Identification of Smallpox Virus," *Journal of Clinical Microbiology*, 42(5): 1940-1946, 2004.

Ropp et al., "PCR strategy for identification and differentiation of small pox and other orthopoxviruses," *Journal of Clinical Microbiology, American Society for Microbiology*, 33(8): 2069-2076, 1995.

Scaramozzino et al, "Real-Time PCR to Identify Variola Virus or Other Human Pathogenic Orthopox Viruses," *Clinical Chemistry*, 53(4): 606-613, 2007.

Supplemental European Search Report, EP Application No. 10828963.8, 12 pages, Jun. 5, 2013.

\* cited by examiner

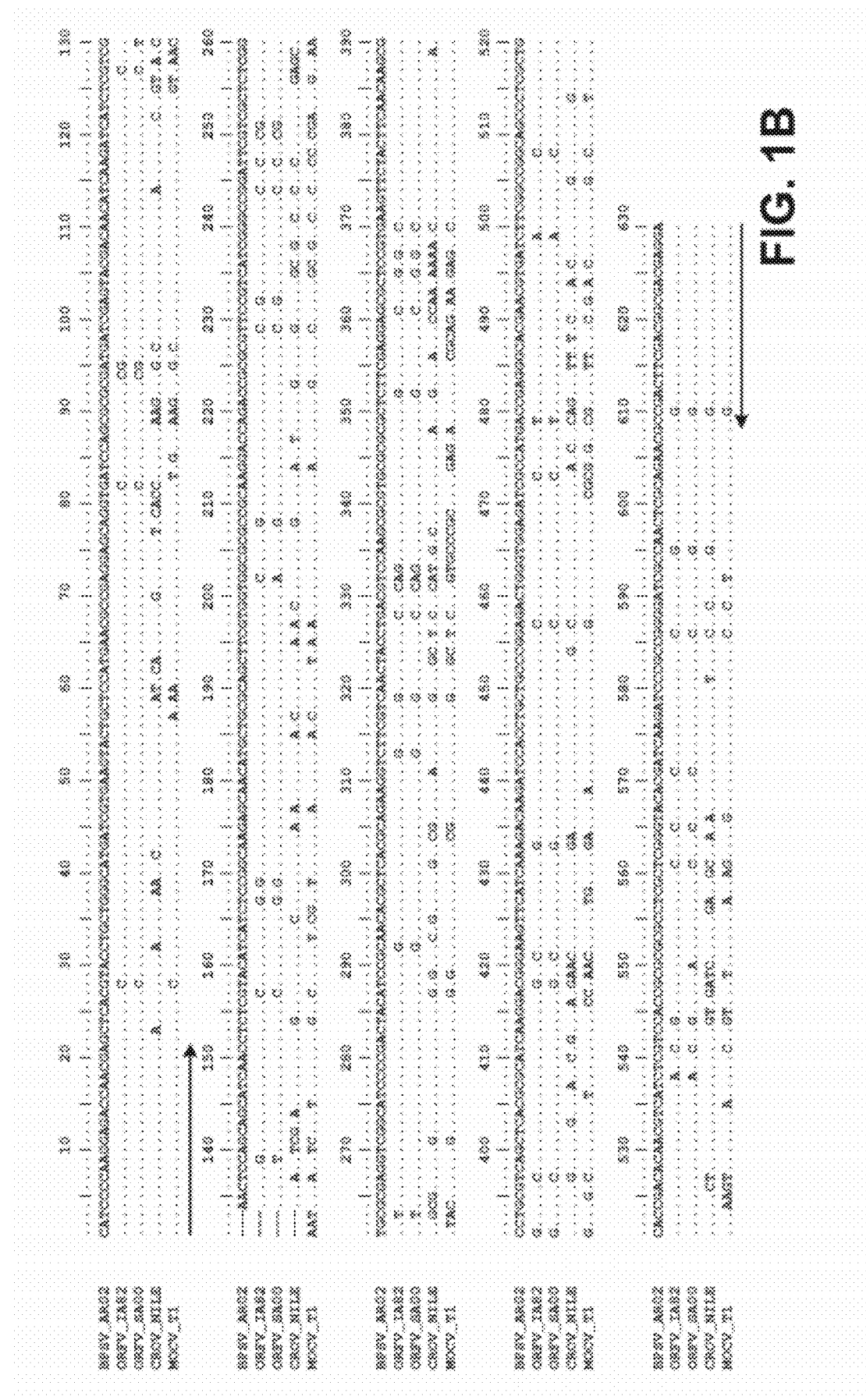

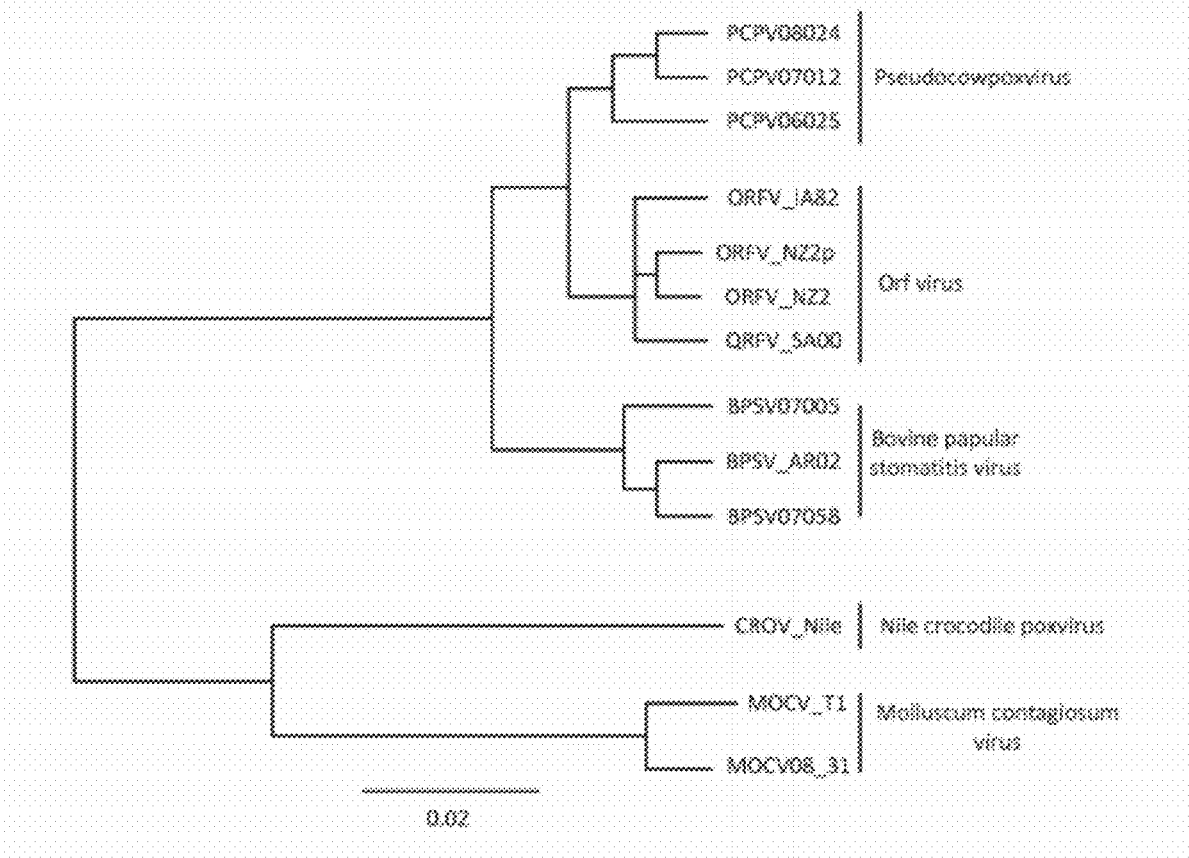

DIAGNOSTIC ASSAYS FOR CHORDOPOXVIRUSES

CROSS REFERENCE TO RELATED APPLICATIONS

This is the U.S. National Stage of International Application No. PCT/US2010/055061, filed Nov. 2, 2010, which was published in English under PCT Article 21(2), which in turn claims the benefit of U.S. Provisional Application 61/257,582 filed Nov. 3, 2009, which is incorporated herein by reference in its entirety.

FIELD

This disclosure relates to compositions and methods of using them in detection and identification of chordopoxvirus(es), such as diagnosis of an infection in a subject.

BACKGROUND

The poxviruses (family Poxyiridae) cause illness characterized by generalized or localized cutaneous lesions and most member viruses have broad host ranges. The overall broad host range of this family is evident by the two subfamilies of the Poxyiridae. The subfamily Entornopoxyirinae infects insects and the subfamily Chordopoxyirinae (chordopoxviruses) infects vertebrates, with the latter encompassing eight classified genera, and other "unclassified chordopoxviruses." The classified genera are: Orthopoxvirus, Parapoxvirus, Avipoxvirus, Capripoxvirus, Leporipoxvirus, Suipoxvirus, Molluscipoxvirus, and Yatapoxvirus.

Poxvirus infections of humans, cattle, sheep, goats, companion animals, birds and zoo animals have been reported worldwide (Damon, "Poxvirus" in *Field Virology* 5th edition, 2947-2976, David M. Knipe, ed.) but in general represent an underappreciated cause of healthcare utilization. Indeed, within the U.S., ICD codes were not available for many of these virus infections until recently. However, the degree to which poxvirus result in patients seeking medical treatment has begun to be defined. One recent study determined that 22/10,000 healthcare visits could be attributed to Molluscum contagiosum infections (Reynolds et. al., *PloS One,* 4:e5255, 2009).

Poxviruses are often the unrecognized source of many emerging or reemerging infections in various parts of the world, and are often clinically confused with other cutaneous diseases. Because the majority of human poxvirus infections are zoonotic, such infections place a significant burden on agricultural communities. Capripoxvirus infections of ruminants cause significant morbidity and mortality. Parapoxvirus infections of ruminants and their handlers are endemic in the U.S. and worldwide; and infected humans often turn to veterinarians for diagnostic assistance (Lederman et al., *Ped. Infect. Dis. J.,* 26:740-744, 2007). In another example, human monkeypox (an orthopoxvirus) is an emerging infection with smallpox-like characteristics that was introduced into the U.S. in 2003 via global commerce in the exotic pet animal trade. The evolution of monkeypox virus and its two major clades in Africa represents an incompletely understood emerging infectious risk. Additionally, although smallpox, caused by variola virus, is an eradicated disease, it remains a significant biothreat agent of international concern, and is the subject of World Health Organization-approved research activities.

Over the past five years, an increasing number of potential poxvirus therapies have been studied. However, better diagnostic methods of identifying poxviruses are necessary in order to determine the cause of cutaneous infections, and decrease their inappropriate treatment. For instance, parapoxvirus infections are often misdiagnosed as cutaneous anthrax, which unnecessarily contributes to overuse of antibacterial agents. There is therefore a demonstrated need to develop better diagnostic tools to detect and identify the agent of poxvirus infections.

SUMMARY

Described herein are compositions for detecting and identifying chordopoxvirus comprising an isolated nucleic acid molecule comprising: an isolated nucleic acid molecule having a sequence at least 80% identical to SEQ ID NO: 13, SEQ ID NO: 14, SEQ ID NO: 20, SEQ ID NO: 21, SEQ ID NO: 22, SEQ ID NO: 23, SEQ ID NO: 25, SEQ ID NO: 26, SEQ ID NO: 28, or SEQ ID NO: 29; an isolated nucleic acid molecule comprising at least 15 consecutive nucleotides of SEQ ID NO: 13, SEQ ID NO: 14, SEQ ID NO: 20, SEQ ID NO: 21, SEQ ID NO: 22, SEQ ID NO: 23, SEQ ID NO: 25, SEQ ID NO: 26, SEQ ID NO: 28, or SEQ ID NO: 29; or an isolated nucleic acid molecule having a sequence selected from the group consisting of SEQ ID NO: 13, SEQ ID NO: 14, SEQ ID NO: 20, SEQ ID NO: 21, SEQ ID NO: 22, SEQ ID NO: 23, SEQ ID NO: 25, SEQ ID NO: 26, SEQ ID NO: 28, and SEQ ID NO: 29.

Also described herein are methods of identifying a chordopoxvirus in a sample that comprises nucleic acids and identifying a virus responsible for a chordopoxvirus infection in a subject by generating an amplicon from the sample using an oligonucleotide primer pair comprising SEQ ID NOs: 13 and 14, or degenerate variants thereof; SEQ ID NOs: 20 and 21, or degenerate variants thereof; SEQ ID NOs: 22 and 23, or degenerate variants thereof; SEQ ID NOs: 25 and 26, or degenerate variants thereof; or SEQ ID NOs: 28 and 29, or degenerate variants thereof; and determining the identity of the amplicon. The identity of the amplicon can be determined by any method known to the art of determining the identity of a nucleic acid including restriction fragment length polymorphism analysis, sequencing, and hybridization to a reference nucleic acid under stringent conditions.

Additionally described are methods of diagnosing an infection of a chordopoxvirus in a subject comprising isolating a sample comprising nucleic acids from the subject and generating an amplicon from the sample using an oligonucleotide primer pair comprising SEQ ID NOs: 13 and 14, or degenerate variants thereof; SEQ ID NOs: 20 and 21, or degenerate variants thereof; SEQ ID NOs: 22 and 23, or degenerate variants thereof; SEQ ID NOs: 25 and 26, or degenerate variants thereof; or SEQ ID NOs: 28 and 29, or degenerate variants thereof, wherein generation of the amplicon diagnoses an infection of a chordopoxvirus infection in the subject.

Lastly described herein are kits for carrying out the described methods comprising: at least one container containing an oligonucleotide primer pair comprising SEQ ID NOs: 13 and 14, or degenerate variants thereof; SEQ ID NOs: 20 and 21, or degenerate variants thereof; SEQ ID NOs: 22 and 23, or degenerate variants thereof; SEQ ID NOs: 25 and 26, or degenerate variants thereof; or SEQ ID NOs: 28 and 29, or degenerate variants thereof; and instructions for identifying or diagnosing a chordopoxvirus in a sample.

The foregoing and other objects, features, and advantages will become more apparent from the following detailed description, which proceeds with reference to the accompanying figures.

BRIEF DESCRIPTION OF THE FIGURES

FIGS. 1A and 1B show sequence alignments of low and high GC PCR amplicons. The names of the viruses corresponding to the abbreviations used in the figure are listed in Table 1. Arrows indicate locations of amplification primers. FIG. 1A shows the alignment of low GC amplicon sequences (SEQ ID NOs: 1-12). 12 predicted amplicon sequences represent 12 species within five chordopoxvirus genera and one unclassified poxvirus. FIG. 1B shows the alignment of high GC amplicon sequences (SEQ ID NOs: 15-19). Five predicted amplicon sequences represent four species of three chordopoxvirus genera and one unclassified poxvirus.

FIGS. 2A and 2B show an agarose gel separation of low and high GC PCR amplicons and their corresponding Taq I RFLP patterns. FIG. 2A shows the amplicons (top panel) and RFLP patterns (bottom panel) of low GC poxviruses in the following lanes: 1. VARV_BSH75, 2. VACV_WR, 3. MPXV_US03_39, 4. CMLV_xx, 5. CPXV_Brt, 6. ETCV_Mos, 7. RPXV, 8. TATV__, 9. VACV__07065, 10. VACV__07070; 11. RACV_MD61, 12. SKPV_WA78, 13. VPXV_CA85, 14. POX_NY014, 15. YMTV_v83, 16. TANV_v93, 17. Cotia virus, 18. MYXV_LAU, 19. RFV_KAS, 20. POX__08040, 21. DPXV_v89. FIG. 2B shows the amplicons (left panel) and RFLP patterns (right panel) of high GC poxviruses in the following lanes: 1. ORFV__06044, 2. ORFV__08041, 3. PCPV__06025, 4. PCPV__08__024, 5. PCPV__07012, 6. PCPV__07013, 7. BPSV__07005, 8. BPSV__07058, 9. MOCV__08031.

FIGS. 3A and 3B illustrate the use of phylogenetic relationships to infer the identity and confirm the diagnosis of poxviruses using the low and high GC PCR sequences. FIG. 3A shows the of low GC PCR amplicon sequences as a way of assigning the new poxvirus isolate Fox_squir (Pox__08040) to the basal of genus Leporipoxviruses and an unknown poxvirus (2001__960) as a distinct clade to all known chordopoxviruses. FIG. 3B shows the phylogeny of high GC PCR amplicon sequences as a way of confirming the clinical diagnoses of parapoxvirus viruses and a molluscum contagiosum virus: the pseudo cowpox virus and bovine papular stomatitis virus clinical isolates form their own clades. MOCV__08031 groups with MOCV_T1 with relative large divergence in comparing the ORFV sequences.

SEQUENCE LISTING

Figure 1A:
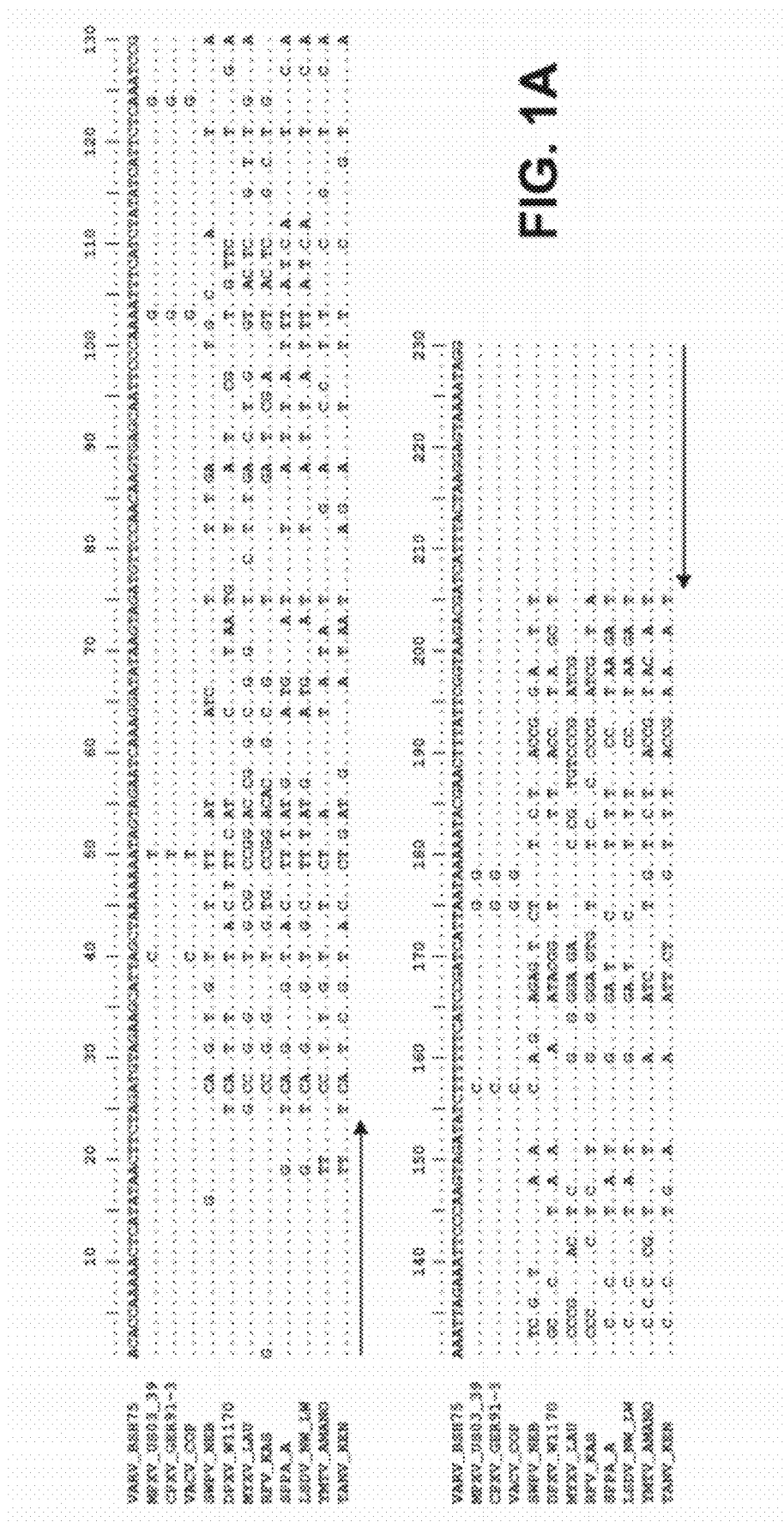

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named seqlist82677-04.txt, created on May 1, 2012, 13.1 KB, which is incorporated by reference herein.

SEQ ID NO: 1 is the nucleotide sequence of the genomic region between the insulin metalloproteinase-like protein and IMV membrane protein genes of Variola major virus strain Bangladesh 1975 VARV_BSH75 (corresponding to positions 61905 to 62134 of genome sequence at GenBank accession No. L22579, the entirety of which is hereby incorporated by reference).

SEQ ID NO: 2 is the nucleotide sequence of the genomic region between the insulin metalloproteinase-like protein and IMV membrane protein genes of Monkeypox virus strain USA__2003__039 MPXV_US03__39 (corresponding to positions 70279 to 70508 of genome sequence at GenBank accession No. DQ011157, the entirety of which is hereby incorporated by reference).

SEQ ID NO: 3 is the nucleotide sequence of the genomic region between the insulin metalloproteinase-like protein and IMV membrane protein genes of Cowpox virus strain Germany 91-3 CPXV_Ger91-3 (corresponding to positions 86519 to 86748 of genome sequence at GenBank accession No. DQ437593, the entirety of which is hereby incorporated by reference).

SEQ ID NO: 4 is the nucleotide sequence of the genomic region between the insulin metalloproteinase-like protein and IMV membrane protein genes of Vaccinia virus strain Copenhagen VACV_COP (corresponding to positions 73674 to 73903 of genome sequence at GenBank accession No. M35027, the entirety of which is hereby incorporated by reference).

SEQ ID NO: 5 is the nucleotide sequence of the genomic region between the insulin metalloproteinase-like protein and IMV membrane protein genes of Swinepox virus strain Nebraska 17077-99 SWPV_Neb (corresponding to positions 45411 to 45539 of genome sequence at GenBank accession No. NC__003389, the entirety of which is hereby incorporated by reference).

SEQ ID NO: 6 is the nucleotide sequence of the genomic region between the insulin metalloproteinase-like protein and IMV membrane protein genes of Deerpox virus strain W-1170-84 DPXV_W1170 (corresponding to positions 58158 to 58387 of genome sequence at GenBank accession No. AY689437, the entirety of which is hereby incorporated by reference).

SEQ ID NO: 7 is the nucleotide sequence of the genomic region between the insulin metalloproteinase-like protein and IMV membrane protein genes of Myxoma virus strain Lausanne MYXV_Lau (corresponding to positions 47776 to 47982 of genome sequence at GenBank accession No. NC__001132, the entirety of which is hereby incorporated by reference).

SEQ ID NO: 8 is the nucleotide sequence of the genomic region between the insulin metalloproteinase-like protein and IMV membrane protein genes of Rabbit fibroma virus strain Kasza RFV_KAS (corresponding to positions 46924 to 47153 of genome sequence at GenBank accession No. NC__001266, the entirety of which is hereby incorporated by reference).

SEQ ID NO: 9 is the nucleotide sequence of the genomic region between the insulin metalloproteinase-like protein and IMV membrane protein genes of Sheeppox virus strain A SPPA_A (corresponding to positions 46216 to 46445 of genome sequence at GenBank accession No. AY077833, the entirety of which is hereby incorporated by reference).

SEQ ID NO: 10 is the nucleotide sequence of the genomic region between the insulin metalloproteinase-like protein and IMV membrane protein genes of Lumpy skin disease virus strain Neethling 2490 LDSV_NW_LW (corresponding to positions 46593 to 46822 of genome sequence at GenBank accession No. NC__003027, the entirety of which is hereby incorporated by reference).

SEQ ID NO: 11 is the nucleotide sequence of the genomic region between the insulin metalloproteinase-like protein and IMV membrane protein genes of Yaba monkey tumor virus strain Amano YMTV_Amano (corresponding to positions 42287 to 42516 of genome sequence at GenBank accession No. NC_005179, the entirety of which is hereby incorporated by reference).

SEQ ID NO: 12 is the nucleotide sequence of the genomic region between the insulin metalloproteinase-like protein and IMV membrane protein genes of Tanapox virus strain Kenya TANV_KEN (corresponding to positions 47754 to 47981 of genome sequence at GenBank accession No. NC_009888, the entirety of which is hereby incorporated by reference).

SEQ ID NOs: 13 and 14 are oligonucleotide sequences for amplifying the genomic sequence between the insulin metalloproteinase-like protein and IMV membrane protein genes of low GC content chordopoxviruses.

SEQ ID NO: 15 is a portion of the nucleotide sequence of a RNA polymerase large subunit gene of Bovine papular stomatitis virus strain BV-AR02BPSV_AR02 (corresponding to positions 55075 to 55701 of genome sequence at GenBank accession No. NC_005337, the entirety of which is hereby incorporated by reference).

SEQ ID NO: 16 is a portion of the nucleotide sequence of a RNA polymerase subunit gene of Orf virus strain OV-IA82 ORFV_IA82 (corresponding to positions 53858 to 54484 of genome sequence at GenBank accession No. AY386263, the entirety of which is hereby incorporated by reference).

SEQ ID NO: 17 is a portion of the nucleotide sequence of a RNA polymerase subunit gene of Orf virus strain OV-SAOO ORFV_SA00 (corresponding to positions 54987 to 55613 of genome sequence at GenBank accession No. NC_005336, the entirety of which is hereby incorporated by reference).

SEQ ID NO: 18 is a portion of the nucleotide sequence of a RNA polymerase subunit gene of Crocodilepox virus strain Zimbabwe CROV_Nile (corresponding to positions 120218 to 120844 of genome sequence at GenBank accession No. NC_008030, the entirety of which is hereby incorporated by reference).

SEQ ID NO: 19 is a portion of the nucleotide sequence of a RNA polymerase subunit gene of Molluscum contagiosum virus strain subtype 1 MOCV_T1 (corresponding to positions 93644 to 94273 of genome sequence at GenBank accession No. NC_001731, the entirety of which is hereby incorporated by reference).

SEQ ID NOs: 20 and 21 are oligonucleotide sequences for amplifying the portion of the genomic sequence encoding a poxvirus RNA polymerase subunit for identification of high GC content chordopoxviruses.

SEQ ID NOs: 22 and 23 are oligonucleotide sequences for amplifying the genomic sequence between the insulin metalloproteinase-like protein and IMV membrane protein genes of Canarypox virus.

SEQ ID NO: 24 is the nucleotide sequence of the genomic region between the insulin metalloproteinase-like protein and IMV membrane protein genes of Canarypox virus (corresponding to positions 110430 to 110662 of genome sequence at GenBank accession No. NC_005309, the entirety of which is hereby incorporated by reference).

SEQ ID NOs: 25 and 26 are oligonucleotide sequences for amplifying the genomic sequence between the insulin metalloproteinase-like protein and IMV membrane protein genes of Fowlpox virus.

SEQ ID NO: 27 is the nucleotide sequence of the genomic region between the insulin metalloproteinase-like protein and IMV membrane protein genes of Fowlpox virus (corresponding to positions 81071 to 81303 of genome sequence at GenBank accession No. NC_002188, the entirety of which is hereby incorporated by reference). SEQ ID NOs: 28 and 29 are oligonucleotide sequences for amplifying the portion of the genomic sequence encoding a poxvirus RNA polymerase subunit for identification of Sealpox virus.

SEQ ID NO: 30 is a portion of the nucleotide sequence of a RNA polymerase subunit gene of Sealpox virus in the amplicon resultant from PCR amplification with SEQ ID NOs: 28 and 29.

DETAILED DESCRIPTION

I. Abbreviations

| bp | base pair(s) |
|---|---|
| BPSV | bovine papular stomatitis virus |
| OPV | Orthopoxvirus |
| ORFV | Orf virus |
| PCPV | Pseudocowpox virus |
| PCR | polymerase chain reaction |
| RFLP | restriction fragment length polymorphisms |
| RT-PCR | reverse transcription polymerase chain reaction |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Animal:

A living multi-cellular vertebrate or invertebrate organism, a category that includes, for example, mammals and birds. The term mammal includes both human and non-human mammals. Similarly, the term "subject" includes both human and veterinary (non-human animal) subjects.

cDNA (Complementary DNA):

A piece of DNA lacking internal, non-coding segments (introns) and transcriptional regulatory sequences. cDNA also may contain untranslated regions (UTRs) that are responsible for translational control in the corresponding RNA molecule. cDNA is synthesized in the laboratory by reverse transcription from messenger RNA extracted from cells.

Degenerate Variant:

A degenerate variant of a probe or primer includes sequences that have altered nucleic acid sequences, but retain their ability to bind to the target sequences (and identify or amplify the target) with sufficient specificity. In some particular examples, no more than about 1, 2, 5, or 10 nucleic acids are changed from the original sequence. In other examples, the probe or primer retains at least 80%, 85%, 90%, 95%, or 98% sequence identity to the original sequence. Degenerate variants also include probe or primer sequences to which additional sequence has been added, while still retaining the noted specificity of the probe or primer.

DNA (Deoxyribonucleic Acid):

DNA is a long chain polymer which comprises the genetic material of most living organisms (some viruses have genomes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Encode:

A polynucleotide is said to encode a polypeptide if, in its native state or when manipulated by methods well known to those skilled in the art, it can be transcribed and/or translated to produce the mRNA for and/or the polypeptide or a fragment thereof.

Fluorophore:

A chemical compound, which when excited by exposure to a particular wavelength of light, emits light (i.e., fluoresces), for example at a different wavelength than that to which it was exposed.

Also encompassed by the term "fluorophore" are luminescent molecules, which are chemical compounds which do not require exposure to a particular wavelength of light to fluoresce; luminescent compounds naturally fluoresce. Therefore, the use of luminescent signals eliminates the need for an external source of electromagnetic radiation, such as a laser. An example of a luminescent molecule includes, but is not limited to, aequorin (Tsien, 1998, *Ann. Rev. Biochem.* 67:509).

Examples of fluorophores are provided in U.S. Pat. No. 5,866,366. These include: 4-acetamido-4'-isothiocyanatostilbene-2,2'disulfonic acid, acridine and derivatives such as acridine and acridine isothiocyanate, 5-(2'-aminoethyl) amino-naphthalene-1-sulfonic acid (EDANS), 4-amino-N-[3-vinylsulfonyl)phenyl]-naphthalimide-3,5 disulfonate (Lucifer Yellow VS), N-(4-anilino-1-naphthyl)-maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethyl-aminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other fluorophores include thiol-reactive europium chelates that emit at approximately 617 n (Heyduk and Heyduk, *Analyt. Biochem.* 248:216-27, 1997; *J. Biol. Chem.* 274:3315-22, 1999).

Other fluorophores include cyanine, merocyanine, stryl, and oxonyl compounds, such as those disclosed in U.S. Pat. Nos. 5,627,027; 5,486,616; 5,569,587; and 5,569,766, and in published PCT application no. US98/00475, each of which is incorporated herein by reference. Specific examples of fluorophores disclosed in one or more of these patent documents include Cy3 and Cy5, for instance, and substituted versions of these fluorophores.

Other fluorophores include GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al., herein incorporated by reference) and derivatives thereof. Other fluorophores are known to those skilled in the art, for example those available from Molecular Probes (Eugene, Oreg.).

Particularly useful fluorophores have the ability to be attached to a nucleotide, such as a modified nucleotide, are substantially stable against photobleaching, and have high quantum efficiency.

Hybridization:

Oligonucleotides and their analogs hybridize by hydrogen bonding, which includes Watson-Crick, Hoogsteen or reversed Hoogsteen hydrogen bonding, between complementary bases. Generally, a nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or IJ, and G will bond to C. Complementary refers to the base pairing that occurs between to distinct nucleic acid sequences or two distinct regions of the same nucleic acid sequence.

One indication that two nucleic acid molecules are closely related is that the two molecules hybridize to each other under stringent conditions. Stringent conditions are sequence-dependent and are different under different environmental parameters.

Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (In *Molecular Cloning: A Laboratory Manual*, Cold Spring Harbor, N.Y., 1989) and Tijssen (*Laboratory Techniques in Biochemistry and Molecular Biology Part I*, Ch. 2, Elsevier, New York, 1993).

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11, herein incorporated by reference. The following is an exemplary set of hybridization conditions:

| Very High Stringency (detects sequences that share 90% identity) |  |
| --- | --- |
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |
| High Stringency (detects sequences that share 80% identity or greater) |  |
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |
| Low Stringency (detects sequences that share greater than 50% identity) |  |
| Hybridization: | 6x SSC at RT to 55° C. for 16-20 hours |
| Wash at least twice: | 2x-3x SSC at RT to 55° C. for 20-30 minutes each. |

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Specifically hybridizable and specifically complementary are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

In Vitro Amplification:

Techniques that increase the number of copies of a nucleic acid molecule in a sample or specimen. An example of in vitro amplification is the polymerase chain reaction (PCR), in which a pair of oligonucleotide primers is added to a sample under conditions that allow for the hybridization of the primers to a nucleic acid template in the sample. The primers are extended under suitable conditions, dissociated from the template, and then re-annealed, extended, and dissociated to amplify the number of copies of the nucleic acid. Other examples of In vitro amplification include, but are not limited to, RT-PCR, quantitative real time PCR, loop mediated isothermal amplification (LAMP), DNA replication, RNA transcription, and primer extension. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated:

An isolated biological component (such as a nucleic acid, peptide or protein) has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been isolated thus include nucleic acids and proteins purified by standard purification methods. The term also embraces nucleic acids, peptides and proteins prepared by recombinant expression in a host cell as well as chemically synthesized nucleic acids. The terms isolated and purified do not require absolute purity; rather, it is intended as a relative term. Thus, for example, an isolated peptide preparation is one in which the peptide or protein is more enriched than the peptide or protein is in its natural environment within a cell.

Label:

A detectable compound or composition that is conjugated directly or indirectly to another molecule to facilitate detection of that molecule. Specific, non-limiting examples of labels include radioactive isotopes, enzyme substrates, co-factors, ligands, chemiluminescent or fluorescent agents, haptens, and enzymes.

Nucleic Acid Molecule:

A polymeric form of nucleotides, which may include both sense and anti-sense strands of RNA, cDNA, genomic DNA, and synthetic forms and mixed polymers thereof. A nucleotide refers to a ribonucleotide, deoxynucleotide or a modified form of either type of nucleotide. A nucleic acid molecule as used herein is synonymous with nucleic acid and polynucleotide. A nucleic acid molecule is usually at least 10 bases in length, unless otherwise specified. The term includes single- and double-stranded forms. A polynucleotide may include either or both naturally occurring and modified nucleotides linked together by naturally occurring and/or non-naturally occurring nucleotide linkages.

Nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and modified linkages (for example, alpha anomeric nucleic acids, etc.). The term nucleic acid molecule also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Unless specified otherwise, the left hand end of a polynucleotide sequence written in the sense orientation is the 5' end and the right hand end of the sequence is the 3' end. In addition, the left hand direction of a polynucleotide sequence written in the sense orientation is referred to as the 5' direction, while the right hand direction of the polynucleotide sequence is referred to as the 3' direction. Further, unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

Oligonucleotide:

A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules and morpholinos.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases. In particular examples, one or more of the constituent nucleotides or nucleotide analogs is labeled, resulting in a labeled oligonucleotide or oligonucleotide analog.

Open Reading Frame:

A series of nucleotide triplets (codons) coding for amino acids without any internal termination codons. These sequences are usually translatable into a peptide.

Poxviruses

A family of double-stranded DNA viruses comprised of two subfamilies defined by host range: the Entomopoxyirinae infect insects and the Chordopoxyirinae (chordopoxviruses) infect vertebrates. As used herein, non-avian chordopoxviruses are all chordopoxviruses except for the avipoxviruses.

Probes and Primers:

Nucleic acid probes and primers can be readily prepared based on the nucleic acid molecules provided in this invention, and therefore provide a substantial utility for the disclosed sequences. A probe comprises an isolated nucleic acid capable of hybridizing to a template nucleic acid, and a detectable label or reporter molecule can be attached to a probe. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed in, for example, Sambrook et al., *Molecular Cloning: A Laboratory Manual*, Cold Spring Harbor Laboratory Press, 2001; and Ausubel et al. (eds.), *Short Protocols in Molecular Biology*, John Wiley and Sons, 1999.

Primers are short nucleic acid molecules, for example DNA oligonucleotides 15 nucleotides or more in length, that in particular examples are labeled in the same manner as probes. Primers can be annealed to a complementary target DNA strand by nucleic acid hybridization to form a hybrid between the primer and the target DNA strand, and the primer can be extended along the target DNA strand by a DNA polymerase enzyme. Primer pairs can be used for amplification of a nucleic acid sequence, e.g., by PCR or other nucleic acid amplification methods.

Methods for preparing and using probes and primers are described, for example, in Sambrook et al.; Ausubel et al. (eds.); and Innis et al., *PCR Applications, Protocols for Functional Genomics*, Academic Press, Inc., 1999. PCR primer pairs can be derived from a known sequence, for example, by using computer programs intended for that purpose such as Primer3, Whitehead Institute for Biomedical Research, Cambridge, Mass.; the program is accessible through the Whitehead Institute's website.

Purified:

In a more pure form than is found in nature. The term purified does not require absolute purity; rather, it is intended as a relative term. Thus, for example, a purified virus preparation is one in which the virus referred to is more pure than the virus in its natural environment within an area of infected tissue.

The term substantially purified as used herein refers to a molecule (for example, a nucleic acid, polypeptide, oligonucleotide, etc.) or virus that is substantially free of other proteins, lipids, carbohydrates, or other materials with which it is naturally associated. In one embodiment, a substantially purified virus is at least 50% free of other proteins, lipids, carbohydrates, or other materials with which it is naturally associated in an area of infected tissue. In another embodiment, the virus is at least at least 80% free of other proteins, lipids, carbohydrates, or other materials with which it is naturally associated in an area of infected tissue. In yet other embodiments, the polypeptide is at least 90% or at least 95% free of other proteins, lipids, carbohydrates, or other materials with which it is naturally associated in an area of infected tissue.

Quantitative Real Time PCR:

A method for detecting and measuring products generated during each cycle of a PCR, which products are proportionate to the amount of template nucleic acid present prior to the start of PCR. The information obtained, such as an amplification curve, can be used to quantitate the initial amounts of template nucleic acid sequence.

Reverse-Transcription PCR (RT-PCR):

A method for detecting, quantifying, or utilizing RNA present in a sample by a procedure wherein the RNA serves as a template for the synthesis of cDNA by a reverse transcriptase followed by PCR to amplify the cDNA. RT-PCR can be used in combination with quantitative real time PCR as a method of measuring the quantity of starting template in the reaction.

Sequence Identity:

The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.* 2: 482, 1981); Needleman and Wunsch (*J. Mol. Biol.* 48: 443, 1970); Pearson and Lipman (*PNAS. USA* 85: 2444, 1988); Higgins and Sharp (*Gene*, 73: 237-244, 1988); Higgins and Sharp (*CABIOS* 5: 151-153, 1989); Corpet et al. (*Nuc. Acids Res.* 16: 10881-10890, 1988); Huang et al. (*Comp. Appls Biosci.* 8: 155-165, 1992); and Pearson et al. (*Meth. Mol. Biol.* 24: 307-31, 1994). Altschul et al. (*Nature*

*Genet.*, 6: 119-129, 1994) presents a detailed consideration of sequence alignment methods and homology calculations.

Subject:

Living multi-cellular organisms, including vertebrate organisms, a category that includes both human and non-human mammals. In particular examples, a subject is any non-avian animal capable of infection by a non-avian chordopoxvirus. In other examples, a subject includes any animal capable of infection by Canarypox virus, Fowlpox virus, or Sealpox virus.

Sample:

Encompasses a sample obtained from an animal, plant, or the environment, whether unfixed, frozen, or fixed in formalin or paraffin. As used herein, samples include all clinical samples useful for detection of viral infection in subjects, including, but not limited to, cells, tissues, and bodily fluids. In particular embodiments, the sample is obtained from an animal subject, such as blood, serum, cerebrospinal fluid, bronchoalveolar levage, pus, or a skin lesion. Samples also include a sample obtained from inanimate objects or reservoirs within an indoor or outdoor environment, including, but not limited to: soil, water, dust, and air samples. In particular examples, a sample is suspected of containing a non-avian chordopoxvirus. In still other examples, it is not necessary to suspect that the sample contains virus.

Under Conditions Sufficient for [Carrying Out a Desired Activity]:

A phrase that is used to describe any environment that permits the desired activity.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Provided herein are compositions for the detection and identification of chordopoxvirus. In one embodiment, the compositions comprise an isolated nucleic acid molecule comprising a sequence at least 80% identical to SEQ ID NO: 13, SEQ ID NO: 14, SEQ ID NO: 20, SEQ ID NO: 21, SEQ ID NO: 22, SEQ ID NO: 23, SEQ ID NO: 25, SEQ ID NO: 26, SEQ ID NO: 28, or SEQ ID NO: 29. In another embodiment the compositions are nucleic acid molecule(s) comprising at least 15 consecutive nucleotides of SEQ ID NO: 13, SEQ ID NO: 14, SEQ ID NO: 20, SEQ ID NO: 21, SEQ ID NO: 22, SEQ ID NO: 23, SEQ ID NO: 25, SEQ ID NO: 26, SEQ ID NO: 28, or SEQ ID NO: 29. In yet another embodiment, the compositions comprise one or more nucleic acid molecules having a sequence selected from the group consisting of SEQ ID NO: 13, SEQ ID NO: 14, SEQ ID NO: 20, SEQ ID NO: 21, SEQ ID NO: 22, SEQ ID NO: 23, SEQ ID NO: 25, SEQ ID NO: 26, SEQ ID NO: 28, and SEQ ID NO: 29. In particular examples, the isolated nucleic acid molecule is an oligonucleotide. In further examples, the isolated nucleic acid further comprises a detectable label.

Also provided herein are methods of identifying a chordopoxvirus in a sample that comprises nucleic acids, the method comprising: generating an amplicon from the sample using an oligonucleotide primer pair comprising SEQ ID NOs: 13 and 14, or degenerate variants thereof; SEQ ID NOs: 20 and 21, or degenerate variants thereof; SEQ ID NOs: 22 and 23, or degenerate variants thereof; SEQ ID NOs: 25 and 26, or degenerate variants thereof; or SEQ ID NOs: 28 and 29, or degenerate variants thereof; and determining the identity of the amplicon; thereby identifying the chordopoxvirus.

In particular examples of the methods of identifying a chordopoxvirus in a sample, at least one of the oligonucleotide primers in the primer pair comprises a detectable label. In other examples, the amplicon comprises at least 80% sequence identity to a sequence selected from the group consisting of SEQ ID NOs: 1-12, SEQ ID NOs: 15-19, SEQ ID NO: 24, SEQ ID NO: 27, and SEQ ID NO: 30. In some examples, determining the identity of the amplicon comprises digesting the amplicon with one or more restriction endonucleases, separating resultant digest products by gel electrophoresis, and detecting a pattern of separated digest products. In other examples, determining the identity of the amplicon comprises sequencing the amplicon and comparing the resultant sequence to at least one reference sequence. In still other examples, determining the identity of the amplicon comprises hybridizing the amplicon under very high stringency conditions to a nucleic acid comprising 15 or more consecutive nucleotides selected from within one of SEQ ID NOs: 1-12, SEQ ID NOs: 15-19, SEQ ID NO: 24, SEQ ID NO: 27, and SEQ ID NO: 30 and detecting the hybridized amplicon; wherein hybridization of the amplicon to a particular sequence indicates the identity of the amplicon.

Additionally provided herein are methods of diagnosing an infection of a chordopoxvirus in a subject comprising isolating a sample comprising nucleic acids from the subject; and generating an amplicon from the sample using an oligonucleotide primer pair comprising SEQ ID NOs: 13 and 14, or degenerate variants thereof; SEQ ID NOs: 20 and 21, or degenerate variants thereof; SEQ ID NOs: 22 and 23, or degenerate variants thereof; SEQ ID NOs: 25 and 26, or degenerate variants thereof; or SEQ ID NOs: 28 and 29, or degenerate variants thereof, wherein generation of the amplicon diagnoses an infection of a chordopoxvirus infection in the subject.

A further embodiment provided are methods identifying a virus responsible for a chordopoxvirus infection in a subject comprising isolating a sample from the subject; and identifying a chordopoxvirus virus in the sample by any other methods described above; thereby identifying the virus responsible for a chordopoxvirus infection in the subject. In particular examples of the methods of diagnosing and identifying a chordopoxvirus, the subject is human. In other examples, the subject is a domestic, companion, farm, or zoo animal. In still other examples, the subject is an animal in the wild.

Further provided herein are kits for carrying out any of the methods described herein comprising: at least one container containing an oligonucleotide primer pair comprising SEQ ID NOs: 13 and 14, or degenerate variants thereof; SEQ ID NOs: 20 and 21, or degenerate variants thereof; SEQ ID NOs: 22 and 23, or degenerate variants thereof; SEQ ID NOs: 25 and 26, or degenerate variants thereof; or SEQ ID NOs: 28 and 29, or degenerate variants thereof; and instructions for identifying or diagnosing a chordopoxvirus in a sample.

IV. Universal ("Pan_Pox") and Species-Specific Primers for Detection of Chordopoxviruses Poxviruses are large, dsDNA viruses that replicate in the cytoplasm of an infected cell. The two subfamilies of poxvirus are broadly defined by host range. Entomopoxyirinae infects insects while Chordopoxyirinae infects vertebrates; the latter family encompasses eight classified genera, and other "unclassified chordopoxviruses". Chordopoxviruses are also grouped by % GC content of their genomic DNA. The genomes of parapoxviruses, molluscipoxviruses and crocodilepox virus (an unclassified poxvirus most similar to molluscipoxvirus) have a high GC content (>60%), while the genomes of the other six genera of chordopoxvirus have a low GC content (30-40%).

The preponderance of data suggests that although the poxviruses can readily recombine in tissue culture conditions (Yao et al. *Virology*, 308:147-156, 2003), they are genomically quite stable in evolutionary time (Li et al., *Proc. Natl. Acad. Sci.*, 104:15787-15792, 2007). Although this relative stability of poxvirus genomic sequence makes the poxviruses suitable for sequence-based methods of identification, methods of universal poxvirus identification have not previously been developed.

Disclosed herein are novel oligonucleotide primers that are effective to detect and identify (and distinguish) non-avian chordopoxviruses. The disclosed "Pan_Pox" primers were developed from the separate genomic sequence alignments of low GC and high GC chordopoxviruses (FIG. 1). Due to its size and degree of sequence variation, Avipoxvirus was excluded from the low GC virus alignment. The disclosed primers correspond to sequences conserved within all non-avian low GC chordopoxviruses (SEQ ID NOs: 13 and 14) and within most GC chordopoxviruses (SEQ ID NOs: 20 and 21), and are capable of generating amplicons from most non-avian chordopoxvirus clinical samples from human and animal infections. A significant advantage of single primer set over multiple primers is that the single primer set amplification (e.g., using PCR) is more likely to amplify previously unknown non-avian chordopoxvirus which fall into the spectrum of a chordopoxvirus subfamily, in both low GC and high GC contents.

As noted above, the genomic sequence alignments for the design of the disclosed Pan_Pox primers excluded the Avipoxviruses (a low GC poxvirus family). Additionally, the high GC Sealpox virus is evolutionarily divergent from the high GC poxviruses used in the described high GC genomic sequence alignment. Thus, also disclosed herein are novel, species-specific oligonucleotide primers that are effective to detect and identify (and distinguish) Canarypox virus (SEQ ID NOs: 22 and 23), Fowlpox virus (SEQ ID NOs: 25 and 26), and Sealpox virus (SEQ ID NOs: 28 and 29).

The Pan_Pox and species-specific primers can comprise any functional or degenerate variant of the disclosed sequences which is still capable of generating a low or high GC content or species-specific amplicon. In some examples, the variant primers are at least 80%, 85%, 90%, 95%, 98% or 99% identical to SEQ ID NOs 13, 14, 20, 21, 22, 23, 25, 26, 28 or 29. In other examples, the variant primers comprise at least 15 consecutive nucleotides of SEQ ID NOs 13, 14, 20, 21, 22, 23, 25, 26, 28 or 29.

In other particular examples, the Pan_Pox or species-specific primers comprise a detectable label. Such labels include any label that can be detected by one of skill in the art, including but not excluded to, radioactive isotopes, enzyme substrates, co-factors, ligands, chemiluminescent or fluorescent agents, or haptens.

V. Detection and Identification of Chordopoxvirus Infection with Pan_Pox or Species-Specific Primers The Pan_Pox primers disclosed herein recognize conserved sequences among most high GC chordopoxviruses, or all non-avian low GC chordopoxviruses. The species-specific primers disclosed herein recognize sequences in Canarypox virus, Fowlpox virus, or Sealpox virus. All of the disclosed primers can generate virus-specific amrplicons which can be identified combining DNA sequencing of the amplicon. Employing these primers, methods have been developed and are described herein for detection and identification of chordopoxviruses. The methods of detection include methods of diagnosis of a viral infection in any subject within the host range of the chordopoxviruses. In particular examples, the subject is human. In other examples the subject is a veterinary subject, including domestic, zoo, or wild veterinary subjects.

In particular examples, the disclosed primers can be used to specifically identify the presence, determine the identity, and/or diagnose the infection of a non-avian chordopoxvirus in a sample. As disclosed herein, the methods of detection of a non-avian chordopoxvirus involve utilizing a pair of (or both pairs of) Pan_Pox primers to generate an amplicon from a sample suspected or known to contain viral particles or viral nucleic acids. The "low GC amplicon" (as that term is used herein) is an approximately 230 bp DNA fragment amplified from viral nucleic acid using the low GC Pan_Pox primers (SEQ ID NOs: 13 and 14), or a degenerate variant thereof. The "high GC amplicon" (as that term is used herein) is an approximately 630 bp DNA fragment amplified from viral nucleic acid using the high GC Pan_Pox primers (SEQ ID NOs 20 and 21), or a degenerate variant thereof. As demonstrated herein, generation of a low or high GC amplicon of the predicted size from a sample indicates the presence of a (high or low GC) non-avian chordopoxvirus in the sample.

In particular examples, amplification of a viral nucleic acid with either Pan_Pox primer pair may not yield a high or low GC amplicon. In such instances, the suspected virus may be identified using the disclosed species-specific primer pairs, or degenerate variants thereof, to identify Canarypox virus (SEQ ID NOs: 22 and 23), Fowlpox virus (SEQ ID NOs: 25 and 26), or Sealpox virus (SEQ ID NOs: 28 and 29). These species-specific primer pairs can be used to generate corresponding species-specific amplicons of about 233 bp (Canarypox and Fowlpox) or about 627 bp (Sealpox). In particular examples wherein the sample is taken from a subject, generation of a low or high GC, or species specific amplicon of the predicted size accurately diagnoses an infection with a non-avian chordopoxvirus of a low or high GC, or corresponding species specific subtype, respectively. In particular examples the sample is taken from the subject in a clinical setting. In other examples the sample is taken from a subject in a non-clinical setting, such as the natural habitat of a non-domesticated animal.

To determine the identity of the chordopoxvirus in the sample, the non-avian specific (low or high GC), or species-specific (Canarypox, Fowlpox or Sealpox) amplicon is further analyzed by any method known to the art for determining the identity of the sequence of the amplicon. In particular examples, the low or high GC, or species-specific amplicon is sequenced. In other examples, the amplicon is digested with one or more restriction endonucleases to generate a strain-specific digest pattern (RFLP analysis). In still other examples, viral identity is determined by hybridization of the amplicon to known viral sequence(s) under very high stringency conditions.

A. Viral and Nucleic Acid Samples

Any samples that are suspected of containing or are known to contain chordopoxvirus particles or viral nucleic acids can provide the viral genomic template used to generate a low or high GC, or species-specific amplicon. In certain examples, such samples are tissue samples from a subject that is suspected of being infected by a chordopoxvirus. In particular examples, the tissue samples are from a subject that is suspected of begin infected by non-avian chordopoxvirus. Tissue samples include any conventional biological sample that can harbor viral particles or nucleic acids, including clinical samples obtained from a human or veterinary subject, for instance blood or blood-fractions (e.g., serum), sputum, saliva, oral or washings, skin scrapes, samples taken from skin lesions, rash pustules, biopsied tissue (for example bronchoscopy samples), bronchoalveolar lavage (BAL) washings, cerebrospinal fluid, or prostate fluid. Standard techniques for acquisition of such samples are available and well known in the art (see, e.g. Schluger et al., *J. Exp. Med.,* 176:1327-1333, 1992; Bigby et al., *Am. Rev. Respir. Dis.,* 133:515-518, 1986; Kovacs et al., *NEJM,* 318:589-593, 1988; and Ognibene et al., *Am. Rev. Respir. Dis.,* 129:929-932, 1984). The sample can be used directly or can be processed, such as by adding solvents, preservatives, buffers, or other compounds or substances. In one example, the sample is used to produce a purified virus preparation. In another example, the sample is used to prepare a stock of virus which is thus isolated from a human or veterinary subject sample.

In one embodiment, nucleic acids are isolated from the sample. DNA or RNA can be extracted from the sample using standard, art recognized methods. For instance, rapid DNA preparation can be performed using a commercially available kit (e.g., the DNeasy Blood & Tissue Kit, Qiagen, Inc., Valencia, Calif.). In another embodiment, a low or high GC amplicon is generated directly from the sample without prior nucleic acid isolation.

B. Low/High GC and Species-Specific Amplicons

The low or high GC, or species-specific amplicon can be generated by any method of amplifying a nucleic acid template through use of oligonucleotide primers, such as the Pan_Pox primers (to generate a non-avian chordopoxvirus amplicon) or the species-specific primers (to generate a Canarypox virus, Fowlpox virus, or Sealpox virus amplicon) disclosed herein. Such methods include, but are not limited to, RT-PCR, quantitative real time PCR, loop mediated isothermal amplification (LAMP), DNA replication, RNA transcription, and primer extension. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

In particular examples, amplification is achieved by conventional PCR. In other examples, wherein RT-PCR is used, PCR amplification with the Pan_Pox or species-specific primers is preceded by reverse transcription of viral RNA. Generation of the amplicon by PCR or RT-PCR can be achieved using any PCR method known to the art. PCR amplification of template sequence can be achieved with any PCR-suitable DNA polymerase under any suitable reaction conditions. One of ordinary skill in the art will be able to optimize the amplification system now that this disclosure has provided the primers to be used.

In particular examples, at least one thermal-stable DNA polymerase is required for PCR generation of a low or high GC, or species-specific amplicon. Any thermal-stable DNA polymerase can be used for PCR generation of the low or high GC amplicon. In particular examples, Taq, Pwo, Tfl, TTh, Tli, or Pfu DNA polymerase is used. In other examples, a combination of polymerases is used.

C. Detection of Amplicons

As demonstrated herein, the presence of a chordopoxvirus in a sample is determined by generation of a low or high GC (for specific detection of non-avian chordopoxvirus), or species-specific (for specific detection of Canarypox virus, Fowlpox virus, or Sealpox virus) amplicon from available template in the sample. The low or high GC, or species-specific amplicon is detected by any method of detecting the generation of DNA by an amplification reaction.

In particular examples, the amplicon-containing sample is separated by agarose gel electrophoresis and the DNA is visualized by ethidium bromide staining. In certain examples the amplicon is labeled through incorporation of a radioactive nucleotide or radioactive labeled primer and is visualized by autoradiography. In other examples, the amplicon is labeled by incorporation of a fluorescent label and is detected spectraphotometrically (Sambrook et al. (In *Molecular Cloning: A Laboratory Manual*, Cold Spring Harbor, N.Y., 1989).

D. Identification of a Poxvirus from the Low or High GC, or Species-Specific Amplicon Sequence As shown in FIG. 1 (and set forth as SEQ ID NOs: 1-12 and 15-19), exemplary sequences of the low or high GC amplicons contain multiple virus-specific sequence variations. In particular embodiments, direct or indirect detection of these differences is used to determine the identity of the non-avian chordopoxvirus in the sample. Any method that can determine the sequence of a nucleic acid or distinguish the sequence of one nucleic acid from another can identify a particular non-avian chordopoxvirus species in the sample from the low or high GC amplicon. Likewise, any method that can determine the sequence of a nucleic acid or distinguish the sequence of one nucleic acid from another can identify, and or verify the identity of a Canarypox virus, Fowlpox virus, or Sealpox virus from the species-specific amplicon generated by the corresponding primer pair. The sequences of these species-specific amplicons are set forth as SEQ ID NO: 24 (Canarypox virus), SEQ ID NO: 27 (Fowlpox virus), and SEQ ID NO: 30 (Sealpox virus).

In one example, the amplicon is sequenced and the sequence is compared to those in a publicly available sequence databases to determine the identity of the virus in the sample. In particular examples, the amplicon sequence will not have 100% sequence identity to the sequence of any previously identified virus. In such examples, the identity of the virus in the sample is inferred from the similarity to sequences in the database (see Example 3) (See Ausubel et al. (eds.), *Current Protocols in Molecular Biology*, published by Wiley InterScience, 2009 (ISSN 1934-3639)).

In another example, the identity of the virus in the sample is determined by RFLP analysis of the amplicon (See Ausubel et al. (eds.), *Current Protocols in Molecular Biology*, published by Wiley InterScience, 2009 (ISSN 1934-3639)). From the sequences shown in SEQ ID NOs: 1-12, SEQ ID NOs: 15-19, SEQ ID NO 24, SEQ ID NO 27, and SEQ ID NO 30, restriction endonuclease cleavage site maps can be generated for each viral species. Such maps can readily be generated using publicly available software such as NEBcutter (Vincze et al., *NAR*, 31: 3688-3691, 2003; available online at tools.neb.com/NEBcutter2/index.php). Based on such predictive maps, one or more restriction endonucleases are selected that will produce species-specific digest patterns from a particular amplicon. In particular examples, the amplicon is digested with at least one restriction endonuclease that has been selected to produce a digestion pattern that can either identify the virus in the sample or narrow the possible identities of the virus in the sample. To positively identify the virus, the resultant digest pattern is compared to those predicted from the known viral sequences. In a particular example, the TaqI enzyme is used for RFLP analysis. Optionally, control samples (e.g., samples containing nucleic acids with known sequence that correspond to one or more of the viral amplicon sequence) are analyzed alongside the text samples to ensure or confirm the quality of analysis results.

In another embodiment, the virus in the sample is identified by hybridization of the generated low or high GC, or species-specific amplicon under very high stringency conditions to a nucleic acid fragment having 15 or more consecutive nucleotides of SEQ ID NOs: 1-12, SEQ ID NOs: 15-19, SEQ ID NO 24, SEQ ID NO 27, or SEQ ID NO 30. Specific hybridization of the amplicon to one of such sequences will indicate the sequence identity of the amplicon and thus, the identity of the virus in the sample.

In some examples, the low or high GC, or species-specific amplicon is tagged with a detectable label and the nucleic acid fragments comprising 15 or more consecutive nucleotides of SEQ ID NOs: 1-12, SEQ ID NOs: 15-19, SEQ ID NO 24, SEQ ID NO 27, or SEQ ID NO 30 are affixed to a solid substrate such as a nylon membrane (for instance, as a probe array). In other embodiments, the nucleic acid fragment comprising 15 or more consecutive nucleotides of SEQ ID NOs: 1-12, SEQ ID NOs: 15-19, SEQ ID NO 24, SEQ ID NO 27, or SEQ ID NO 30 is tagged with a detectable label and the amplicon in affixed to a solid substrate such as a nylon membrane.

VI. Identification and Classification of Unknown Chordopoxviruses

The Pan_Pox primers described herein are capable of generating a specific amplicon in all known non-avian chordopoxvirus species. However, it is understood that not all such viruses have been identified or sequenced. Thus, with the primers disclosed herein, it is possible to detect a non-avian chordopoxvirus species that does not share 100% sequence identity with any previously identified and sequenced non-avian chordopoxvirus.

In such instances, the evolutionary relationship between the unknown and known viruses can be determined through sequencing of the generated amplicon and analysis of the sequence using software such as the Bayesian analysis software package, (BEAST, BEAUti, and Trace (Drummond and Rambaut, *BMC. Evol. Biol.*, 7:214, 2007)) to determine the similarities in sequence and thus the phylogenetic relationship between the previously-unknown virus and those that have been characterized. See, for instance, Example 3 and FIGS. 3 and 4 for an illustration of the categorization of a previously unidentified virus using the Pan_Pox primers.

VII. High Throughput Screening

The disclosed methods for diagnosis and identification of chordopoxvirus infection can be used to screen a large numbers of samples simultaneously (that is, can be used in high-throughput applications). In particular examples, such high-throughput screening is accomplished through generating the low or high GC, or species-specific amplicon by PCR amplification. In particular examples, this method is carried out by any of the numerous methods to process multiple amplification reactions (See Ausubel et al. (eds.), *Current Protocols in Molecular Biology*, published by Wiley InterScience, 2009 (ISSN 1934-3639)). Such methods include, but are not limited to, amplification in a thermal cycler compatible with a microtiter plate, use of an automated liquid handling and thermal cycler workstation, or other high throughput techniques such as that according to Morrison et al. (*Nucl. Acids Res.,* 34: e123, 2006). Optionally, the equivalent high-throughput liquid handling techniques are then used for batch RFLP or sequencing analysis of the generated amplicons in order to determine virus identity from the amplicon sequence.

VIII. Kits

This disclosure also provides kits that enable a user to diagnose and/or identify chordopoxvirus infections. Such kits contain at least one or more containers of Pan_Pox, or species-specific primers. In particular examples, the primers are provided in individual containers. In other examples, mixtures of the high or low GC, or species specific primer pairs are provided in a single container. In some examples, the kits are specific for diagnosis/identification of high GC chordopoxviruses. In other examples, the kits are specific for diagnosis/identification of low GC non-avian chordopoxvirus. In still other examples, the kits are specific for diagnosis/identification of Canarypox virus, Fowlpox virus, or Sealpox virus. Kits can optionally provide instructions for carrying out disclosed methods of diagnosing and identifying chordopoxvirus infections. In particular examples, the kits would additionally include reagents useful in generating the low and/or high GC, or species-specific amplicon, such at least one type of thermal-stable DNA polymerase, nucleotides and/or buffers necessary for PCR amplification of a DNA sequence.

Certain kits include reagents useful for identification of specific strains of poxvirus from the low or high GC, or species-specific amplicon. Examples of such kits include at least one type of restriction endonuclease for use in RFLP analysis of the low or high GC amplicon. Other example kits include reagents useful for sequencing the amplicon.

The materials provided in such kits may be provided in any form practicable, such as suspended in an aqueous solution or as a freeze-dried or lyophilized powder, for instance. Kits according to this disclosure can also include instructions, usually written instructions, to assist the user in carrying out the detection and identification methods disclosed herein. Such instructions can optionally be provided on a computer readable medium or as a link to an internet page.

The container(s) in which the reagents are supplied can be any conventional container that is capable of holding the supplied form, for instance, microfuge tubes, ampoules, or bottles. In some applications, the Pan_Pox or species-specific primers, thermal-stable nucleic acid polymerase(s), restriction endonuclease(s), or other reagent mixtures useful for diagnosis and identification of chordopoxvirus infection may be provided in pre-measured single use amounts in individual, typically disposable, tubes, microtiter plates, or equivalent containers. The containers may also be compatible with a specific automated liquid handling apparatus.

The amount of a reagent supplied in the kit can be any appropriate amount, depending for instance on the market to which the product is directed. For instance, if the kit is adapted for research or clinical use, the amount of each reagent, such as the Pan_Pox or species-specific primers, thermal-stable nucleic acid polymerase(s), or restriction endonuclease(s) would likely be an amount sufficient for multiple screening assays. In other examples where the kit is intended for high throughput industrial use, the amounts could be sufficiently increased to accommodate multiple hundreds of assays.

The following examples are provided to illustrate certain particular features and/or embodiments. These examples should not be construed to limit the invention to the particular features or embodiments described.

EXAMPLES

Example 1

Generation of "Pan_Pox" and Species-Specific Primers to Identify and Distinguish Chordopoxviruses Chordopoxviruses are subdivided by % GC content into low (30-40%) and high GC content (>60%). This example shows the development of "Pan_Pox" PCR primers specific for universal identification of viruses within each of the low GC and high GC content groups. Also described is the development of species-specific primers for specific identification of Canarypox, Fowlpox and Sealpox viruses which are evolutionarily divergent from those viruses identifiable by the Pan_Pox primers.

Methods

Viral Genome Sequence Alignment:

A multiple sequence alignment program MAFFT (Katoh et al., *Nucleic Acids Res.*, 30:3059-3066, 2002) was used for the alignment of poxvirus genome sequences. The conserved sequences from multiple genome sequence alignment were studied manually for the design of pan-poxvirus PCR primers. The sequence editing and alignment from high and low (C PCR amplicons used the DNASTAR Lasergene 8 software package (DNASTAR, Inc., Madison, Wis.) and BioEdit software (on-line at mbio.ncsu.edu/BioEdit/bioedit.html).

Design of Primers for Low GC Content Virus Identification:

Viral genomes from genera with high GC content were aligned separately from those with low GC content (FIG. 1). Design of PCR primer sequences to identify low GC content poxviruses was based on the sequence alignment of low GC content poxviruses listed in Table I (top). The conserved sequences were screened and analyzed by considering the sequence specificity, annealing temperature, and potential secondary structure formation with the assistant of Primer Express (version 1.5; Applied Biosystems) software. The selected forward primer hybridizes within the insulin metalloproteinase-like protein gene: ACACCAAAAACT-CATATAACTTCT (SEQ ID NO: 13). The selected reverse primer hybridizes within the IMV membrane protein gene: CCTATTTTACTCCTTAGTAAATGAT (SEQ ID NO: 14).

Table 1 lists two avipoxviruses, Canarypox and Fowlpox, among the low GC content poxviruses. However, as discussed below, Avipoxvirus genomes are widely divergent from other low GC content genomes. Thus, Avipoxvirus genomes were excluded from the low GC content alignment. To detect Canarypox and Fowlpox virus in a sample, primers were designed based on sequence analysis of Canarypox and Fowlpox insulin metalloproteinase-like protein and IMV membrane protein gene orthologs. As with the Pan_Pox primers, the selected forward and reverse primers hybridize within the insulin metalloproteinase-like protein and IMV membrane protein genes, respectively. The selected Canarypox forward primer is ACACCAAAAACTCATATAAGTGC (SEQ ID NO: 22), and the selected Canarypox reverse primer is TTATTTTACCATTAATTAAATGAT (SEQ ID NO: 23). The selected Fowlpox forward primer is ACACCA-GAAACTCATATACGTAC (SEQ ID NO: 25), and the selected Fowlpox reverse primer is CTTATTTTAACTG-TACTTAAATGAT (SEQ ID NO: 26).

Design of Primers for High GC Content Virus Identification:

Design of PCR primer sequences to identify high GC poxviruses was based on the available genome sequences of poxvirus strains with high GC content (listed in Table 1, bottom). A selection criterion similar to the low GC PCR primers was used for the primer selection. Both of the primers selected hybridize to a subunit of the poxvirus RNA polymerase. The sequence of the forward primer is: CATC-CCCAAGGAGACCAACGAG (SEQ ID NO: 20); and the sequence of the reverse primer is: TCCTCGTCGCCGTC-GAAGTC (SEQ ID NO: 21).

Sealpox virus is a high GC poxvirus that is evolutionarily divergent from the poxviruses used in the high GC content genome alignment. Thus, Sealpox virus cannot be identified using the primers designed from the high GC content genome alignment. To detect Sealpox virus, primers were designed based on sequence analysis of the Sealpox virus ortholog of the same subunit of the poxvirus RNA polymerase used in designing the Pan_Pox high GC poxvirus identification primers. As with the Pan_Pox primers, the selected forward and reverse primers hybridize within the RNA polymerase subunit. The selected Sealpox forward primer is CATTC-CAAAAGAAACAAACGAACTT (SEQ ID NO: 28), and the selected Sealpox reverse primer is TCTTCGTCTCCGT-CAAAGTCAGC (SEQ ID NO: 29).

TABLE 1

Selected Chordopoxvirus strains representing different genus and GC content

| | Genus | Species | Abbrev. | GenBank No. | Size (bases) | G + C % |
|---|---|---|---|---|---|---|
| Low GC | Capripoxvirus | Goatpox virus strain G20-LKV | | AY077836 | 149,723 | 25.3 |
| | | Lumpy skin disease virus strain Neethling 2490 | LSDV_NW_LW | NC_003027 | 150,773 | 25.9 |
| | | Sheeppox virus strain A | SPPA_A | AY077833 | 150,057 | 25 |
| | Leporipoxvirus | Myxoma virus strain Lausanne | MYXV_Lau | NC_001132 | 161,773 | 43.6 |
| | | Rabbit fibroma virus strain Kasza | RFV_KAS | NC_001266 | 159,857 | 39.5 |
| | Orthopoxvirus | Camelpox virus strain CMS | | AY009089 | 202,205 | 33.2 |
| | | Cowpox virus strain Germany 91.3 | CPXV_Ger91-3 | DQ437593 | 228,250 | 33.5 |
| | | Ectromelia virus stain Moscow | | NC-004105 | 209,771 | 33.2 |

TABLE 1-continued

Selected Chordopoxvirus strains representing different genus and GC content

| | Genus | Species | Abbrev. | GenBank No. | Size (bases) | G + C % |
|---|---|---|---|---|---|---|
| | | Monkeypox virus strain USA_2003_039 | MPXV_US03_39 | DQ011157 | 198,780 | 33.1 |
| | | Taterapox virus strain Dahomey 1968 | | NC_008291 | 198,050 | 33.3 |
| | | Vaccinia virus strain Western Reserve | | NC-006998 | 194,711 | 33.4 |
| | | Vaccinia virus strain Copenhagen | VACV_COP | M35027 | 191,738 | 33.4 |
| | | Variola major virus strain Bangladesh 1975 | VARV_BSH75 | L22579 | 186,103 | 32.7 |
| | Suipoxvirus | Swinepox virus strain Nebraska 17077-99 | SWPV_Neb | NC_003389 | 146,454 | 27.4 |
| | Yatapoxvirus | Tanapox virus strain Kenya | TANV_KEN | NC_009888 | 144,565 | 27 |
| | | Yaba monkey tumor virus strain Amano | YMTV_Amano | NC_005179 | 134,721 | 29.8 |
| | Unclassified Poxviridae | Deerpox virus strain W-1170-84 | DPXV_W1170 | AY689437 | 170,560 | 27 |
| | Avipoxvirus | Canarypox virus strain ATCC_VR111 | | NC_005209 | 359,853 | 30.4 |
| | | Fowlpox virus strain Iowa | | NC_002188 | 288,539 | 30.9 |
| High GC | Molluscipoxvirus | Molluscum contagiousum virus strain subtype 1 | MOCV_T1 | NC_001731 | 190,289 | 63.4 |
| | Parapoxvirus | Bovine popular stomatitis virus strain BV-AR02 | BPSV_AR02 | NC_005337 | 134,431 | 64.5 |
| | | Orf virus strain OV-SA00 | ORFV_SA00 | NC_005336 | 139,962 | 64.3 |
| | | Orf virus strain OV-IA82 | ORFV_IA82 | AY386263 | 137,241 | 64.3 |
| | Unclassified Poxviridae | Crocodilepox virus strain Zimbabwe | CROV_Nile | NC_008030 | 190,054 | 61.9 |

Results

Genome Sequence Alignment of Chordopoxviruses

A new multiple sequence alignment program MAFFT was used to align poxvirus genome sequences (Katoh et al., *Nucleic Acids Res.*, 33:511-518, 2005). MAFFT constructed initial alignments by the progressive method and finished alignments using the iterative refinement methods which improved the speed of the alignment of large, complex genome sequences of multiple genera of poxviruses. The genome sequences alignment of each virus genus used is depicted (FIG. 1). The entomopoxviruses genome sequences were not included in the analysis as they diverged significantly from chordopoxviruses with considerable gene order rearrangement. Within the chordopoxvirus subfamily, avipoxviruses have the largest genome and are more diverged from other genera of chordopoxviruses. In addition, avipoxvirus genomes contain multiple rearrangements in comparison to other chordopoxviruses which introduced numerous gaps in the genome sequence alignments which reduced the quality of the alignment results. Thus, for the low GC sequence alignment, avipoxvirus genomes were not included.

The results of the genome sequence alignments were manually studied to identify the suitable primer targets. The low GC PCR assay target selected spans a portion of insulin metalloproteinase-like protein (forward primer, G1L ortholog (SEQ ID NO: 13)) to the IMV membrane protein gene (reverse primer G3L ortholog (SEQ ID NO: 14)), and generates an amplicon about 230 bp in size (FIG. 1A) (SEQ ID NOs: 1-12). The primer annealing site sequences are conserved except for a single nucleotide variation in the SWPV_NEB and RFV_KAS forward primer annealing site. Neither variation is expected to affect the PCR amplification of those DNA. Alignment of low GC primer sequences with Avipoxvirus genomes using BLAST sequence analysis software (available online at: blast.ncbi.nlm.nih.gov/Blast.cgi) shows that the primer annealing target sequences have limited homology and the target size changed significantly, suggesting that the low GC PCR could not amplify Avipoxvirus DNA. Therefore, the sequences of the Canarypox and Fowlpox orthologs of the insulin metalloproteinase-like protein and IMV membrane protein genes were analyzed to design primers for PCR identification of viral DNA in a sample. PCR amplification with the selected Canarypox virus primers (SEQ ID NOs: 22 and 23) is expected to yield an amplicon of 233 bp in length, as set forth in SEQ ID NO: 24). PCR amplification with the selected Fowlpox virus primers (SEQ ID NOs: 25 and 26) is expected to yield an amplicon of 233 bp in length, as set forth in SEQ ID NO: 27).

Genome sequences with high GC content are limited; most sequences are from genus of parapoxvirus, plus one genome from genus of Molluscipoxvirus and an unclassified poxvirus: Crocodilepoxvirus. The high GC PCR assay target is of the RNA polymerase subunit gene (J6R, a vaccinia virus strain Copenhagen ortholog). The primer sequences (SEQ ID NOs: 20 and 21) are conserved between the aligned high GC content viruses, and are predicted to generate a 630 bp amplicon. (FIG. 1B) (SEQ ID NOs: 15-19). Analysis of the unpublished Sealpox virus genome indicated that the primers designed from the high GC content genome alignment will not identify the evolutionary divergent high GC content Sealpox virus. Therefore, the sequence of the Sealpox virus ortholog of the subunit of the poxvirus RNA polymerase subunit used to design the high GC content amplification primers was analyzed to design primers for PCR identification of Sealpox virus DNA in a sample. PCR amplification with the selected Sealpox virus primers (SEQ ID NOs: 28 and 29) is expected to yield an amplicon of 627 bp in length, as set forth in SEQ ID NO: 30).

Example 2

Identification of Poxviruses with the Low and High GC Content Primers

This example confirms the prediction made from analysis of available chordopoxvirus sequences predicting that the low and high GC "Pan_Pox" PCR primers can be used to detect and identify all low GC content poxviruses (except avipoxvirus) and most high GC content poxviruses. Also shown is confirmation of the efficacy of the described Sealpox identification primers at identifying Sealpox DNA in a sample.

Methods

Viruses and DNA Preparation

The origins of the viruses and methods for preparing DNA from purified virions or infected cell cultures are described elsewhere (Esposito et al., *J. Virol. Meth.*, 2:175-179, 1981; Espositio et al., *Virology*, 142:230-251, 1985; Esposito et al., *Virology*, 89:53-66, 1978; Knight et al., *Virology*, 190:423-433, 1992; Li et al., *J. Clin. Virol.*, 36:194-203, 2006; Massung et al., *Virology*, 201:215-240, 1994; Reed et al., *N. Engl. J. Med.*, 350:342-305, 2004; Ropp, *J. Clin. Microbiol.*, 33:206-2076, 1995). DNA from the CDC poxvirus collection was used for assay development.

In initial validation of low GC PCR assay, ten Eurasian or Old World orthopoxviruses were used (including a monkeypox virus (MPXV_US03_39), a cowpox virus (CPX-V_BRT), a variola virus (VARV_BSH75), a laboratory vaccinia virus (VACV_WR), a rabbit poxvirus (RPXV), an ectromelia virus (ETCV_MOS), a camelpox virus (CM-LV_v78), a taterapoxvirus (TATV_DAH68), and two recent vaccinia virus human clinical samples (VACV_07065, VACV_07070) (CDC, *MMWR*, 57:401-404, 2008)); along with three North American orthopoxviruses (including a Racoonpox virus (RACV_MD61), a Volepox virus (VPX-V_CA85), and a Skunkpox virus (SKPV_WA78)); two Leporipoxviruses (myxoma virus (MYXV_LAU) and Rabbit fibroma virus (RFV_Kas)); two Yatapoxviruses (Yaba monkey tumor virus (YMTV_v83) and Tanapox virus (TANV_04)) (Dhar et al., *N. Engl. J. Med*, 350:361-366, 2004); three unclassified poxviruses (Cotia virus—from South America (Esposito et al., *J. Gen. Virol.*, 47:37-46, 1980; Lopesode et al., *Am. J. Trop. Med. Hyg.*, 14:156-157, 1965), a clinical isolate NY 014 from New York state, and a North America deer poxvirus DPXV_v89)); and a nucleic acid sample extracted from a fox squirrel body lesion (POX_08040).

The development of the high GC PCR assay utilized nucleic acids extracted from clinical specimens of parapoxviruses including two orf viruses from Missouri (ORFV_06044, ORFV_08041); four pseudocowpox viruses from Missouri (PCPV_06025), West Virginia (08024), and Bangladesh (PCPV_07005, PCPV_07006); two bovine papular stomatitis viruses from Bangladesh (BPSV_07012) and Washington (BPSV_07058); and molluscum contagiosum virus (MOCV_08031). Separate validation of the efficacy of the Sealpox identification primers utilized nucleic acids isolated from a stock Sealpox virus sample (Sealpox_SP19).

PCR Conditions:

Primers were made by β-cyanoethyl phosphoramidite chemistry (Sinha et al., *Nucleic Acids Res*, 12:4539-4557, 1984) using a Model 380B Oligonucleotide Synthesizer (Applied Biosystems, Foster City, Calif.). The software PRIME (Accelrys GCG, San Diego, Calif.) was used to assess primer melting temperatures and dimerization capacities.

The validation PCR assays were set up as follows: PCR mixtures contained-10-100 ng of viral DNA and 20 µM of a primer pair in 50 µl of a solution of 50 mM Tris-HCl buffer (pH 9.2), 16 mM $(NH_4)_2SO_4$, 2.25 mM $MgCl_2$, 2% (v/v) dimethylsulfoxide, 0.1% (v/v) detergent Tween 20, 350 µM each of dATP, dCTP, dGTP, and dTTP, and 2 Units of the DNA polymerases Taq and Pwo provided in the Expand Long Template PCR Kit (Roche Molecular Biologicals, Indianapolis, Ind.). For PCR amplification, we used a Model 9700 thermocycler (Perkin-Elmer Cetus, Boston, Mass.) programmed as follows: after 2 minutes at 92° C. for DNA denaturing, reaction mixtures were thermocycled 10 times through successive denaturing (92° C. for 10 seconds), annealing (50° C. (low GC primers) or 65° C. (high GC primers) for 30 seconds), and elongation (68° C. for 1 minute) steps, and then through 20 cycles of denaturing, annealing, and elongation in which each successive elongation step added 2 seconds. Four µl were inspected for the amplicon size by electrophoresis in 4% E-gel (Invitrogen-Novex, Carlsbad, Calif.) run at 30 minutes in without buffer (pre-loaded with ethidium bromide). PCR products were stored at 4° C.

RFLP Analysis:

A four base cutter restriction endonuclease Taq I (5' TCGA 3' New England Biolabs, Beverly, Mass.) was used to generate RFLP profiles to differentiate amplicons of different viruses: the PCR amplicons were digested with 2 Units of Taq I in 10 µl reaction mixtures incubated at 65° C. at a minimum 1 hour. To visualize the restriction fragments, 5 µl of each digest were separated by a 4% E-gel (Invitrogen-Novex, Carlsbad, Calif.) run at 30 minutes in without buffer (pre-loaded ethidium bromide) The Fluor-S system (Bio-Rad, Hercules, Calif.) was used to create gel digital photo images in Tagged Image File Format (TIFF).

DNA Sequencing:

The low and high GC PCR amplicons were sequenced after PCR product clean-up using the ExoSAP-IT kit (USB, Cleveland, Ohio). PCR products were incubated at 37° C. for 15 minutes, followed at 80° C. for 15 minutes to inactive the enzymes The purified products (0.2-0.5 µg) were sequenced in separate 10 µl reaction mixtures containing 1 mmol each of an oligonucleotide primer pair and 4 µl BigDye Terminator v3.1 cycle sequencing RR-100 reagent (Applied Biosystems, Foster City, Calif.). Mixtures were thermocycled 35 times at 96° C. for 10 seconds, 50° C. for 5 seconds, and 60° C. for 1 minute. The reaction products were clarified using DycEx 2.0 Spin kit (QIAGEN, Valencia, Calif.). Then 20 µl of Hi-Di Formamide (Applied Biosystems, Foster City, Calif.) was added to 10 µl of purified sequencing reaction products. Samples were loaded capillary electrophoresis system (Model 3130X1 Genetic Analyzer, Applied Biosystems, Foster City, Calif.).

Results

Low GC Content PCR Assay Validation

Figures 2A, 2B:
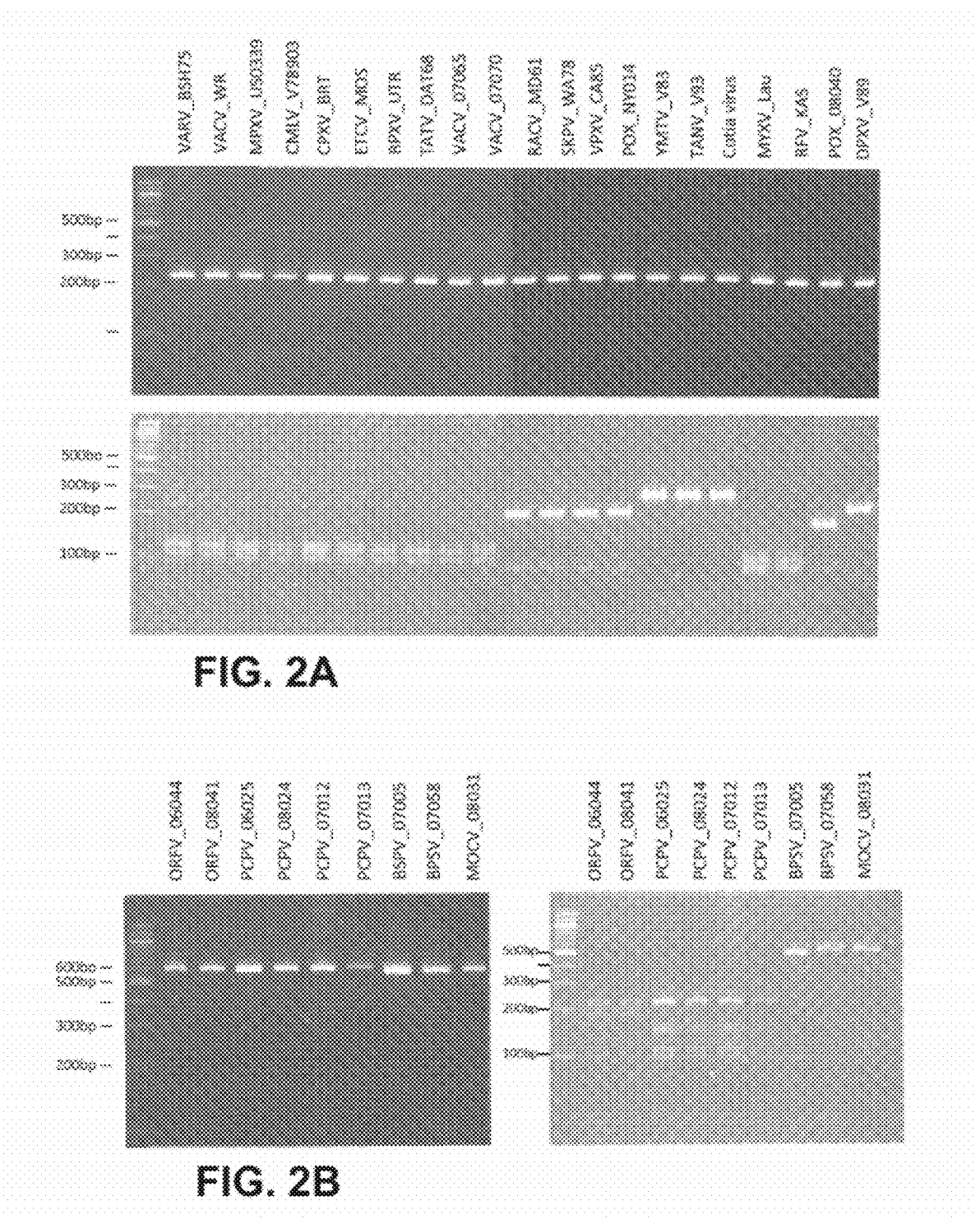

The initial validation used partially purified poxvirus DNAs. As expected, the low GC primers did not amplify the high GC poxvirus DNAs. The low GC PCR assay amplified an appropriately sized amplicon from all the poxvirus isolates, or clinical materials, with known low GC content tested (FIG. 2A). This included ten Eurasia OPV, three North America OPV, two Leporipoxviruses, two Yatapoxviruses, three unclassified poxviruses, and a new poxvirus isolate from a fox squirrel lesion. Concordant with the sequence alignment (FIG. 1A), the amplicon size is similar among the isolates in different genera (FIG. 2A, top).

Restriction fragment length polymorphism (RFLP) analysis of the amplicons with Taq I restriction endonuclease digestion provided a convenient way to differentiate between some genera or species (FIG. 2A, bottom). All Eurasian OPV yielded an identical double band (about 127 and 107 nucleotides in size). North American OPV also yielded double bands but the sizes of those bands (about 170 and 64 nucleotides in size) are different from Eurasia OPV.

The newly discovered poxvirus NY_014 and a deerpox virus DPXV_v89 from North America have a similar RFLP pattern to that of North America OPV. The two Yatapoxvirus and the unclassified Cotia virus are not cleaved by TaqI. TaqI cleavage of the two leporipoxvirus amplicons produced multiple small fragments. TaqI cleavage of the amplicon generated from the fox squirrel poxvirus lesion also produced multiple bands, but the banding pattern sizes were not identical to those derived from the two leporipoxviruses, myxoma and RFV.

High GC Content PCR Assay Validation.

The high GC PCR assay was designed to amplify the known high GC content poxviruses: parapoxvirus, Molluscum contagiosum virus, and Crocodilepox virus strain Zimbabwe.

Neither parapoxvirus nor Molluscum contagiosum virus is easily propagated in immortalized cell culture systems. For the validation of high GC PCR assay by PCR amplification and sequencing confirmation, nucleic acid isolated directly from parapoxvirus and Molluscum contagiosum virus clinical samples was used. Two ORFV, four PCPV and two BPSV, and one Molluscum contagiosum virus DNA were amplified (FIG. 2B, left).

The corresponding Taq I RFLP patterns are unique for each species and agree with the RFLP patterns predicted from virus sequences. The RFLP patterns of BPSV isolates are similar to that of MOCV_08031 as predicted by sequence. In comparison, the predicted Taq I RFLP pattern of MOCV_08031 has a variation to that of MOCV_T1. The sequences show that MOCV_08031 is about 97% identical to MOCV type (FIG. 2B, right).

Figure 4:
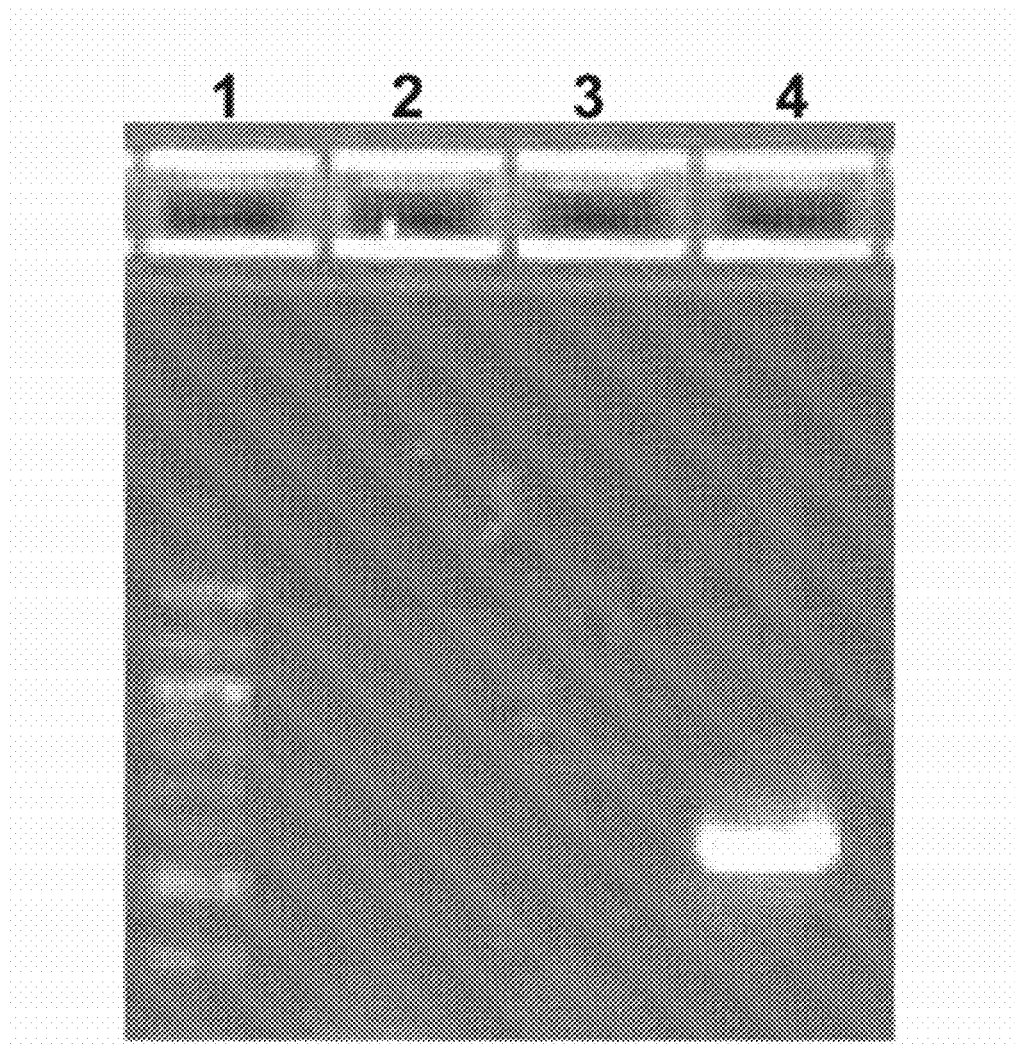
FIG. 4 shows an agarose gel separation of PCR amplification products generated using species-specific primers for detection of Sealpox virus. Lane 1 is a 100 base pair (bp) molecular weight standard starting at 400 bp, and with 500 and 1000 bp having twice the intensity. Lane 4 shows the amplicon generated using Sealpox virus DNA as the template.

For the validation of the Sealpox virus identification primers, isolated Sealpox virus DNA was amplified as described above. As shown in FIG. 4, PCR amplification of yielded a single amplicon of predicted size, confirming the efficacy of the selected primers.

Evaluation of the Pan_Pox Assays with a Large Collection of Poxvirus Isolates.

The low and high GC PCR assays were further tested with 146 poxviruses including nucleic acids directly extracted from swinepox, crocodilepox, and Molluscum contagiosum virus clinical materials (listed in Table 2).

The low GC PCR assay was able to amplify Orthopoxviruses, including 8 camelpox, 78 cowpox, 17 monkeypox, 8 mousepox, 14 vaccinia, and 1 raccoonpox virus isolates; Capripoxviruses, including1 lumpy skin disease virus, 1 sheeppox virus; Suipox virus, 1 swinepox virus DNA; and Yatapoxviruses including1 tanapox virus, and 1 yaba-like disease virus.

The high GC PCR assay was able to amplify DNA from 13 Parapoxvirus isolates including, 9 Orf viruses; 2 bovine papular stomatitis viruses, 1 pseudocowpoxvirus, and 1 camel parapoxvirus species; and 1 Molluscum contagiosum, and 1 crocodilepoxvirus.

TABLE 2

The low GC (A) and high GC (B) poxviruses identified using Pan_Pox the PCR assay

| Genus | Strain ID | Species | Host | Country | Year |
|---|---|---|---|---|---|
| A. Low GC Poxvirus Isolates | | | | | |
| Orthopoxvirus | 1230/95 Haut | Camelpox virus | Camel | Dubai | 1995 |
| | 1231/95 Haut | Camelpox virus | Camel | Dubai | 1995 |
| | 1260/95 Haut | Camelpox virus | Camel | Dubai | 1995 |
| | C-269/96 | Camelpox virus | Camel | Dubai | 1996 |
| | CP-298-2 Wildtype | Camelpox virus | Camel | Dubai | |
| | CP-Syrien | Camelpox virus | Camel | Syria | 2005 |
| | Niger VD 49 | Camelpox virus | Camel | Niger | |
| | CP-19 | Camelpox virus | Camel | Dubai | 1994 |
| | Cowpox Gießen A | Cowpox virus | | Germany | |
| | KR-1 | Cowpox virus | | The Netherlands | |
| | Kuhpocken ch. 659 | Cowpox virus | | Germany | |
| | Katzenbär | Cowpox virus | Bearcat | Germany | 1997 |
| | Biber V940/97 | Cowpox virus | Beaver | Germany | 1997 |
| | OPV02 (m1) | Cowpox virus | Callithrix | Germany | 2002 |
| | 277/03 | Cowpox virus | Cat | Germany | 1999 |
| | 69/01 | Cowpox virus | Cat | Germany | 2001 |
| | 81/01 | Cowpox virus | Cat | Germany | 2001 |
| | 867-99b | Cowpox virus | Cat | Austria | 1999 |
| | Cat Pox 3L97 | Cowpox virus | Cat | United Kingdom | 1983 |
| | Catpox Utrecht | Cowpox virus | Cat | The Netherlands | |
| | K1639 | Cowpox virus | Cat | United Kingdom | 2000 |
| | K2739 | Cowpox virus | Cat | United Kingdom | 2000 |
| | K2984 | Cowpox virus | Cat | United Kingdom | 2000 |
| | K4207 | Cowpox virus | Cat | United Kingdom | 2000 |
| | K427 | Cowpox virus | Cat | United Kingdom | 2000 |
| | K428 | Cowpox virus | Cat | United Kingdom | 2000 |
| | K779 | Cowpox virus | Cat | United Kingdom | 2000 |
| | K780 | Cowpox virus | Cat | United Kingdom | 2000 |
| | Katze Hannover S 1936/07 | Cowpox virus | Cat | Germany | 2007 |
| | Katze Hannover S2216/04 | Cowpox virus | Cat | Germany | 2005 |
| | Norway feline | Cowpox virus | Cat | Norway | 1995 |
| | OPV 88 Haut lidil | Cowpox virus | Cat | Germany | 1988 |
| | OPV 88 Lunge lidil | Cowpox virus | Cat | Germany | 1988 |
| | OPV 89/1 | Cowpox virus | Cat | Germany | 1989 |
| | OPV 89/2 | Cowpox virus | Cat | Germany | 1989 |
| | OPV 89/3 Calw | Cowpox virus | Cat | Germany | 1989 |
| | OPV 89/5 Haut/Klon 4 | Cowpox virus | Cat | Germany | 1989 |
| | OPV 89/5 Lunge | Cowpox virus | Cat | Germany | 1989 |
| | OPV 90/3 | Cowpox virus | Cat | Germany | 1990 |
| | OPV 90/5 | Cowpox virus | Cat | Germany | 1990 |

TABLE 2-continued

The low GC (A) and high GC (B) poxviruses identified using Pan_Pox the PCR assay

| Genus | Strain ID | Species | Host | Country | Year |
|---|---|---|---|---|---|
| | OPV 98/3 | Cowpox virus | Cat | Germany | 1998 |
| | OPV 90/1 | Cowpox virus | Cat | Germany | 1990 |
| | 91/1 Rind | Cowpox virus | Cattle | Germany | 1991 |
| | Catpox 5/WV-1 | Cowpox virus | Cheetah | United Kingdom | 1982 |
| | Elef. Virus Holl 2501 | Cowpox virus | Elephant | The Netherlands | |
| | Elef. Virus Holl 3297 "Suzula" | Cowpox virus | Elephant | The Netherlands | 1973 |
| | Elefauntenhaut Gießen | Cowpox virus | Elephant | Germany | 1989 |
| | Elefantp. Magdeburg | Cowpox virus | Elephant | Germany | |
| | EP Wein | Cowpox virus | Elephant | Austria | 1974 |
| | EP Wutzler | Cowpox virus | Elephant | Germany | 1988 |
| | EP-1 | Cowpox virus | Elephant | Germany | 1971 |
| | EP-2 lidil | Cowpox virus | Elephant | Germany | 1975 |
| | EP-3 lidil | Cowpox virus | Elephant | Germany | 1977 |
| | EP-4 lidil | Cowpox virus | Elephant | Germany | 1980 |
| | EP-5 | Cowpox virus | Elephant | Germany | 1988 |
| | EP-6 (EP-Berlin) | Cowpox virus | Elephant | Germany | 1998 |
| | EP-7 | Cowpox virus | Elephant | Germany | 2000 |
| | EP-8 | Cowpox virus | Elephant | Germany | 2000 |
| | EP-Riems | Cowpox virus | Elephant | Germany | 1980 |
| | Kuhpocken Hamburg | Cowpox virus | Elephant | Germany | 1984 |
| | Kuhpocken Tubingen | Cowpox virus | Elephant | Germany | 1979 |
| | OPV 98/5 | Cowpox virus | Horse | Germany | 1998 |
| | Haut Mensch | Cowpox virus | Human | Germany | 2007 |
| | 000536 | Cowpox virus | Human | United Kingdom | 2003 |
| | Brighton VR 302 | Cowpox virus | Human | United Kingdom | 1937 |
| | 28/00 | Cowpox virus | Human | Germany | 2000 |
| | 65/01 | Cowpox virus | Human | Germany | 2001 |
| | 66/01 | Cowpox virus | Human | Germany | 2001 |
| | 75/01 | Cowpox virus | Human | Germany | 2001 |
| | Fin 3081 | Cowpox virus | Human | Finland | 2000 |
| | Girl | Cowpox virus | Human | The Netherlands | 2002 |
| | Nancy | Cowpox virus | Human | France | 2001 |
| | Norway human | Cowpox virus | Human | Norway | 1995 |
| | OPV 05/1 | Cowpox virus | Human | France | 2005 |
| | OPV 85 lidil | Cowpox virus | Human | Germany | 1985 |
| | OPV 98/2 | Cowpox virus | Human | Germany | 1998 |
| | Schwede III | Cowpox virus | Human | Sweden | 2001 |
| | Schwede IV | Cowpox virus | Human | Sweden | 2005 |
| | Udine | Cowpox virus | Human | Italy | 2006 |
| | Vis 1971-90 (Schwe I) | Cowpox virus | Human | Sweden | 1990 |
| | Vis 2058-90 (Schwe II) | Cowpox virus | Human | Sweden | 1990 |
| | OPV 90/4 | Cowpox virus | Hund | Germany | 1990 |
| | Okapi | Cowpox virus | Okapi | Germany | |
| | Rat | Cowpox virus | Rat | The Netherlands | 2002 |
| | Nashornpocken ch. 15 | Cowpox virus | Rhino | | |
| | 275/03 | Cowpox virus | Tapir | Germany | 1999 |
| | AP-5 WRAIR | Monkeypox virus | Cynomolgus | DRC | 1971 |
| | 04MPX095c | Monkeypox virus | Human | DRC | |
| | 04MPX099v | Monkeypox virus | Human | DRC | 2004 |
| | 06MPX0575v | Monkeypox virus | Human | DRC | 2006 |
| | 06MPX0609v | Monkeypox virus | Human | DRC | 2006 |
| | 06MPX0699c | Monkeypox virus | Human | DRC | 2006 |
| | 06MPX0727c | Monkeypox virus | Human | DRC | 2006 |
| | 06MPX0739c | Monkeypox virus | Human | DRC | 2006 |
| | 06MPX0743c | Monkeypox virus | Human | DRC | 2006 |
| | 06MPX0785c | Monkeypox virus | Human | DRC | 2006 |
| | 06MPX0802v | Monkeypox virus | Human | DRC | 2006 |
| | 06MPX0850v | Monkeypox virus | Human | DRC | 2006 |
| | 06MPX0854c | Monkeypox virus | Human | DRC | 2006 |
| | MSF#10 | Monkeypox virus | Human | DRC | 2001 |
| | MSF#2 | Monkeypox virus | Human | DRC | 2001 |
| | MSF#6 | Monkeypox virus | Human | DRC | 2001 |
| | AP-4, 65-31 | Monkeypox virus | Monkey | DRC | 1965 |
| | Blaufuchs | Mousepox virus | Fox | Czech Republic | 1993 |
| | LTK Moskau | Mousepox virus | Mouse | Russia | |
| | MP C99-505 | Mousepox virus | Mouse | United States | 1999 |
| | MP-1 | Mousepox virus | Mouse | Germany | 1983 |
| | MP-3 | Mousepox virus | Mouse | Germany | |
| | US # 33221 | Mousepox virus | Mouse | United States | 1995 |
| | US #4908 | Mousepox virus | Mouse | United States | 1995 |
| | US Organ 9 | Mousepox virus | Mouse | United States | 1995 |
| | ATCC VR 838 | Raccoon poxvirus | Raccoon | United States | |
| | Elstree "Wyeth" NYCBHL | Vaccinia virus | | | |
| | Copenhagen host range | Vaccinia virus | | | |
| | Copenhagen wildtype | Vaccinia virus | | | |

TABLE 2-continued

The low GC (A) and high GC (B) poxviruses identified using Pan_Pox the PCR assay

| Genus | Strain ID | Species | Host | Country | Year |
|---|---|---|---|---|---|
| | CVA Plague 7 | Vaccinia virus | | | |
| | Hagen Lidil | Vaccinia virus | | | |
| | Holland Vaccine | Vaccinia virus | | | |
| | IHD | Vaccinia virus | | | |
| | Levaditi | Vaccinia virus | | | |
| | WR | Vaccinia virus | | | |
| | Büffelpocken ch. 3 | Vaccinia virus | Buffalo | | |
| | Büffelpox BP-1 lidil | Vaccinia virus | Buffalo | | |
| | 144/89/K. | Vaccinia virus | Human | Germany | 1989 |
| | 170/05 Büffelpox | Vaccinia virus | Human | Pakistan | 2005 |
| | 35/99 | Vaccinia virus | Human | Germany | 1999 |
| Capripoxvirus | Lumpy Skin | Lumpy skin disease virus | | | |
| | Sheeppox Vaccine | Sheeppox virus | | | |
| Suipoxvirus | Schweinepox | Swinepox virus | Swine | | |
| Yatapoxvirus | Tanapox | Tanapox virus | | | |
| | Yaba like Davis strain | Yaba-like disease virus | Monkey | | |
| B. High GC Poxvirus Isolates | | | | | |
| Parapoxvirus | MM 7.KOP | Orf virus | Human | Germany | 1996 |
| | B014 | Orf virus | Human | Germany | 1996 |
| | ORF | Orf virus | Sheep | | |
| | Orf 11 | Orf virus | Sheep | Scotland | 1996 |
| | B032 Namibia | Orf virus | Sheep | Namibia | 2003 |
| | B047 6. BEL | Orf virus | Goat | Germany | 1987 |
| | NZ-2 | Orf virus | Sheep | New Zealand | 1982 |
| | S1 Japan | Orf virus | Sheep | Japan | 1985 |
| | B020 15 µl | Orf virus | Goat | Germany | 2004 |
| | V590/75 | Bovine papular stomatitis | Cattle | Germany | 1979 |
| | Kamerun 21 | Bovine papular stomatitis | Cattle | Cameroon | 2002 |
| | B035 | Pseudocowpoxvirus | Cattle | Germany | 2004 |
| | CE 48 | Camel parapox virus | Camel | Sudan | 2006 |
| Molluscipoxvirus | Molluscum contagiosum | Molluscum contagiosum virus | Human | Germany | 2008 |
| Unclassified | Crocopox | | Crocodile | | |

Example 3

Use of Universal (Pan_Pox) Primers to Identify/Classify Unknown Poxvirus and Poxvirus Infections This example demonstrates the utility of the Pan_Pox primers for identification and classification of suspected or unclassified poxviruses.

Methods

Amplification and analysis of poxvirus DNA using the low GC and high GC PCR primers was as described in Example 2.

Phylogenetic Analysis of Sequences of PCR Amplicons:

The phylogeny of clinical poxvirus specimens was inferred utilized the Bayesian analysis software package, BEAST, BEAUti, and Trace (Drummond and Rambaut, *BMC Evol Biol*, 7:214, 2007). The analyses run MCMC chain length of 5,000,000-10,000,000 (until EES value>100) with an HKY+ Gamma (categories 4)+ Invariant sites nucleotide rate substitution model with fixed mean substitution rate at the 1.0, and sampling of every 1,000 states.

Results

Diagnostics for Suspected Poxvirus Clinical Samples or Unknown Rash Specimens.

The low and high GC PCR assays were used to successfully aid in the identification of suspected poxviruses in a variety of animal-derived rash specimens. The newly discovered poxvirus NY_014, which caused a progressive panniculitis in an immune suppressed patient was amplified by the low GC PCR primers. A DNA sample (Pox_08040) extracted from a fox squirrel (*Sciurus niger*) with multiple nodular lesions was tested to rule out the possible infection with the oral rabies vaccine (a live vaccinia-rabies glycoprotein recombinant virus) (Hanlon et al., *J. Wildl. Dis.*, 34:228-239, 1998). The CDC standard orthopoxvirus and vaccinia specific real-time PCR assays did not amplify DNA derived from the sample (Li, *J. Clin. Virol.*, 36:194-203, 2006). In contrast, the low GC PCR primers described herein amplified the DNA. Analysis of the amplicon sequence shows that the infection was caused by a Lepripoxvirus-like poxvirus, perhaps related to the squirrel fibroma virus which was first reported by King et al. over 35 years ago (King et al., *J. Wildl. Dis.*, 8:321-324, 1972).

Figure 3A:
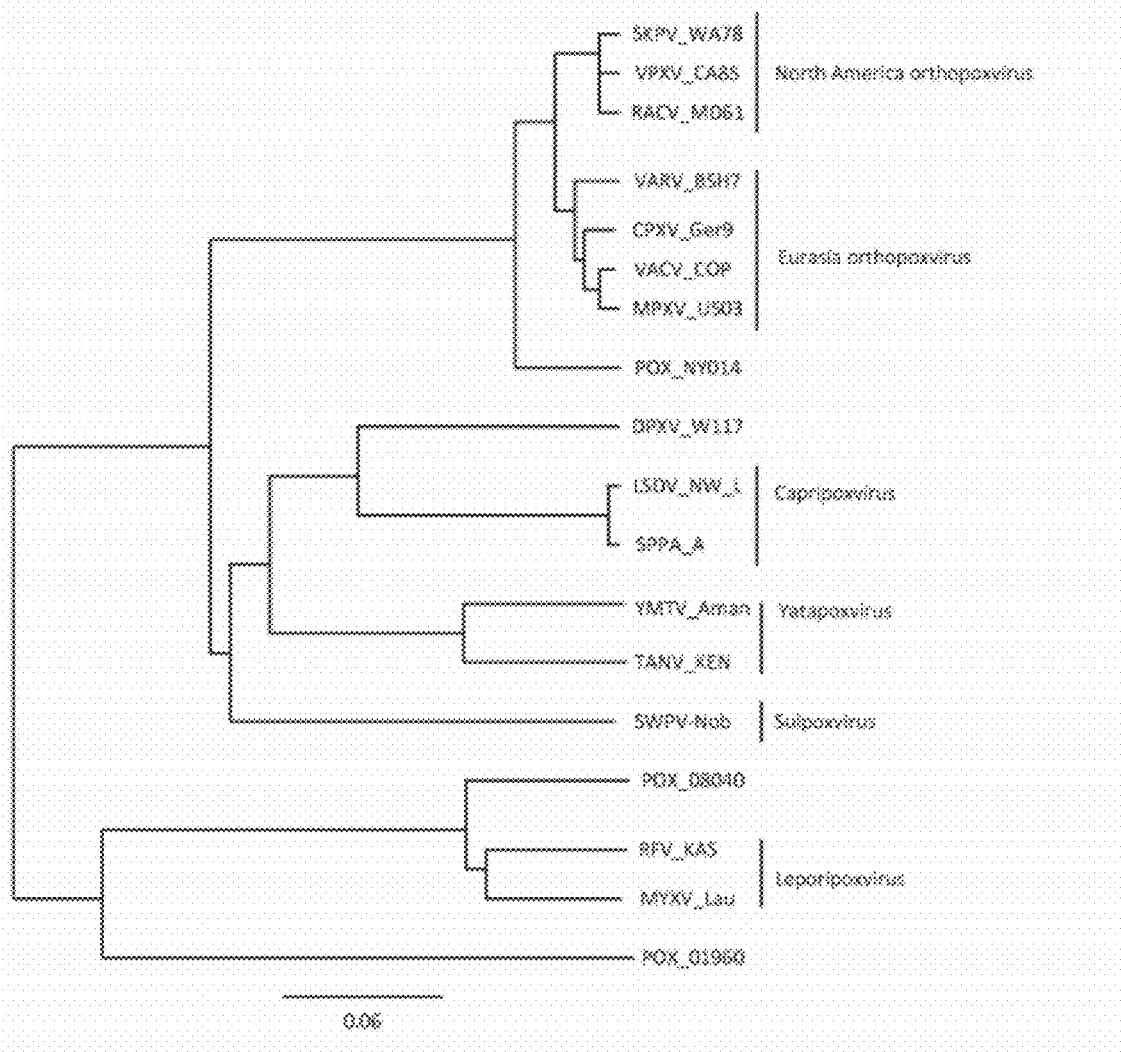

The low GC PCR assay also identified a new poxvirus (2001_960) from nucleic acid extracted from formalin fixed tissue of a skin lesion from a rat that had come into contact with a child who developed a febrile rash illness in the Northwestern United States. The amplicon-derived sequence did not have significant identity to any nucleotide sequences in a BLAST GenBank search but has the highest similarity to Molluscum contagiosum virus subtype 1 (MCV) at the amino acid level. Interestingly, MCV has a high GC content. Thus, this result may support the cladogram which suggests that sample 2001_960 contains a virus which is a member of a new genus of chordopoxvirus, as it forms a distinct clade (FIG. 3A).

Sample MOCV_08031 was obtained from a specimen initially suspected to be a herpes virus infection. The high GC PCR primers amplified an amplicon from the clinical sample, and the sequences of the amplicon identified it as a Molluscum contagiosum like virus. The MCV has at least three subtypes (Porter and Archard, *J Med Virol,* 38:1-6, 1992). The sequence of the amplicon derived from the clinical sample MOCV_08031 is 3% divergent based on nucleic acid content relative to MOCV subtype I (FIG. 3B), which may indicate it is another MOCV subtype. The high GC PCR primers amplified three PCPV isolates and two BPSV isolates that were initially diagnosed as PCPV and BPSV respectively using real-time PCR assays. Comparative sequence analysis of the amplicons generated by the high GC PCR primers was concordant with the prior real time PCR assay results, and additionally indicated that PCPV and BPSV contain subclades, as does ORFV (FIG. 3B).

Example 4

Identification of Poxviruses by Hybridization of the Low or High GC Amplicon to Known Viral Sequences This example describes the identification of a poxvirus in a sample by hybridization of a generated low or high GC, or species-specific amplicon to a known viral sequence under very high stringency conditions.

Using the Pan_Pox primers described herein (e.g., SEQ ID NOs: 13 and 14 or 20 and 21), a low or high GC amplicon is generated from available template in a sample. The amplicon can be tagged with a detectable label either during or following its generation. The labeled amplicon is then hybridized under very high stringency conditions to a nucleic acid molecule that comprises at least 15 consecutive nucleotides from one of SEQ ID NOs 1-12 (if a low GC amplicon) or SEQ ID NOs: 15-19 (if a high GC amplicon).

If amplification of a suspected poxvirus sample with the Pan_Pox primers does not yield an expected amplicon, the suspected poxvirus might be Canarypox, Fowlpox, or Sealpox virus. Positive identification of virus in a sample as one of these three non-Pan_Pox identifiable viruses is achieved as above, except PCR amplification is carried out using the virus-specific primers described herein for Canarypox (SEQ ID NOs: 22 and 23), Fowlpox (SEQ ID NOs: 25 and 26), and Sealpox (SEQ ID NOs: 28 and 29). The generated amplicon can be tagged with a detectable label either during or following its generation. The labeled amplicon is then hybridized under very high stringency conditions to a nucleic acid molecule that comprises at least 15 consecutive nucleotides from one of SEQ ID NO: 24 (for a Canarypox amplicon), SEQ ID NO: 27 (for a Fowlpox amplicon), or SEQ ID NO: 30 (for a Sealpox amplicon).

Optionally, the above-described hybridization may occur in an array format, where the amplicon is allowed to hybridize to an array of possible target sequences. Detection of a labeled amplicon that is hybridized to a particular sequence (for instance, at a particular address on an array) indicates the identity of the amplicon, and thus the identity of the virus in the sample.

Example 5

High Throughput Identification of Poxviruses with Pan_Pox and Species-Specific Primers This example describes representative uses of the disclosed technology to assay for chordopoxvirus infection in a subject or sample by various high throughput methods, which permit screening through numerous samples utilizing the low and high GC Pan_Pox primers and the Canarypox, Fowlpox, and Sealpox virus primers described herein.

Using an automated, semiautomated, or manual liquid handling device, tissue samples containing suspected virus or DNA isolated from suspected viral samples may be dispensed into part or all of a microtiter plate. Using the same liquid handling methods, the method of generating amplicons from viral DNA and identifying a particular poxvirus from the generated amplicons is performed as described herein (with art-recognized modifications for high throughput and/or miniaturized systems). Concomitant use of a thermal cycler adapted to the particular microtiter plate format will allow for batch processing of nucleic acid amplification, RFLP analysis, or sequencing of generated amplicons.

Example 6

Diagnosis of Chordopoxvirus Infection

The Pan_Pox and species-specific primers disclosed herein can be used to diagnose and/or identify most suspected poxvirus infections in a vertebrate subject, including humans, zoo animals, companion animals, domestic animals and wild animals, that presents symptoms of a febrile rash illness. This example describes one way in which the Pan_Pox and species-specific PCR primers can be used for diagnosis and identification.

For diagnosis and/or identification of poxvirus infection, a tissue sample is taken from any subject (e.g., human or veterinary) in any context (e.g., clinical or non-clinical). DNA is then isolated from the sample and used as the template to generate the low or high GC amplicon using the low GC or high GC content primers described herein. The described species-specific primers for identification of Canarypox, Fowlpox, or Sealpox can be additionally used in instances of suspected infection with the corresponding viruses or when the low of high GC amplicon is not generated.

The generated amplicon (low or high GC or species-specific) is then detected, for instance by gel electrophoresis, and the presence of such an amplicon indicates infection of the subject hy a non-avian low GC chordopoxvirus, non-avian high GC chordopoxvirus. Canarypox virus, Fowlpox virus, or Sealpox virus.

The identity of Ihe causative agent of the specific poxvinis infection is determined as described herein by identifying the sequence or distinguishing sequence characteristics of the generated amplicon (see lixample 2. for instance I, lixemplary methods of such analysis are RII.I* analysis, DNA sequencing, and hybridization under very high stringency conditions to particular poxvirus sequences, from results of such methods, the identity of the particular chonhipoxvims is extrapolated as described in Examples 2-4.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A pair of isolated nucleic acid molecules, the respective sequences of which:
   consist of SEQ ID NOs: 13 and 14;
   consist of SEQ ID NOs: 20 and 21;
   consist of SEQ ID NOs: 22 and 23;
   consist of SEQ ID NOs: 25 and 26;
   consist of SEQ ID NOs: 28 and 29; or
   comprise SEQ ID NO: 28 and comprise a nucleic acid sequence at least 95% identical to SEQ ID NO: 29,
   wherein at least one of the pair of isolated nucleic acid molecules is operably linked to a detectable label and wherein the detectable label comprises a radioactive isotope, a chemiluminescent or fluorescent agent, a hapten, or an enzyme.

2. The pair of isolated nucleic acid molecules of claim 1, wherein the nucleic acid molecules are oligonucleotides.

3. A method of identifying a chordopoxvirus in a sample that comprises nucleic acids, the method comprising:
   generating an amplicon from the sample using a pair of oligonucleotide primers, the respective sequences of which:
   consist of SEQ ID NOs: 13 and 14;
   consist of SEQ ID NOs: 20 and 21;
   consist of SEQ ID NOs: 22 and 23;
   consist of SEQ ID NOs: 25 and 26;
   consist of SEQ ID NOs: 28 and 29; or
   comprise SEQ ID NO: 28 and comprise a nucleic acid sequence at least 95% identical to SEQ ID NO: 29; and
   determining the identity of the amplicon;
   thereby identifying the chordopoxvirus in the sample.

4. The method of claim 3, wherein at least one of the oligonucleotide primers in the primer pair comprises a detectable label, and wherein the detectable label comprises a radioactive isotope, a chemiluminescent or fluorescent agent, a hapten, or an enzyme.

5. The method of claim 3, wherein the amplicon comprises at least 80% sequence identity to a sequence selected from the group consisting of SEQ ID NOs: 1-12, SEQ ID NOs: 15-19, SEQ ID NO: 24, SEQ ID NO: 27, and SEQ 6. The method of claim 3, wherein determining the identity of the amplicon comprises:

digesting the amplicon with one or more restriction endonucleases;

separating resultant digest products by gel electrophoresis; and detecting a pattern of separated digest products.

7. The method of claim 3, wherein determining the identity of the amplicon comprises:

sequencing the amplicon; and comparing the resultant sequence to at least one reference sequence.

8. The method of claim 3, wherein determining the identity of the amplicon comprises:

hybridizing the amplicon under very high stringency conditions to a nucleic acid comprising 15 or more consecutive nucleotides selected from within one of SEQ ID NOs: 1-12, SEQ ID NOs: 15-19, SEQ ID NO: 24, SEQ ID NO: 27, and SEQ ID NO: 30; and detecting the hybridized amplicon;

wherein hybridization of the amplicon to a particular sequence indicates the identity of the amplicon.

9. A method of diagnosing an infection of a chordopoxvirus in a subject comprising:

isolating a sample comprising nucleic acids from the subject; and generating an amplicon from the sample using a pair of oligonucleotide primers, the respective sequences of which:

consist of SEQ ID NOs: 13 and 14;

consist of SEQ ID NOs: 20 and 21;

consist of SEQ ID NOs: 22 and 23;

consist of SEQ ID NOs: 25 and 26;

consist of SEQ ID NOs: 28 and 29; or comprise SEQ ID NO: 28 and comprise a nucleic acid sequence at least 95% identical to SEQ ID NO: 29; and wherein generation of the amplicon diagnoses an infection of chordopoxvirus in the subject.

10. A method of identifying a virus responsible for a chordopoxvirus infection in a subject comprising:

isolating a sample from the subject; and identifying a chordopoxvirus virus in the sample by the method of claim 7, thereby identifying the virus responsible for the chordopoxvirus infection in the subject.

11. The method of claim 9, wherein the subject is human.

12. The method of claim 9, wherein the subject is a domestic, companion, farm, or zoo animal.

13. The method of claim 9, wherein the subject is an animal in the wild.

14. A kit for carrying out the method of claim 3, comprising:

at least one container containing a pair of oligonucleotide primers, the respective sequences of which:

consist of SEQ ID NOs: 13 and 14;

consist of SEQ ID NOs: 20 and 21;

consist of SEQ ID NOs: 22 and 23;

consist of SEQ ID NOs: 25 and 26;

consist of SEQ ID NOs: 28 and 29; or comprise SEQ ID NO: 28 and comprise a nucleic acid sequence at least 95% identical to SEQ ID NO: 29; and wherein at least one oligonucleotide in the oligonucleotide primer pair is operably linked to a detectable label, and wherein the detectable label comprises a radioactive isotope, a chemiluminescent or fluorescent agent, a hapten, or an enzyme; and instructions for identifying a chordopoxvirus in a sample.

15. A kit for carrying out the method of claim 9, comprising:

at least one container containing a pair of oligonucleotide primers, the respective sequences of which:

consist of SEQ ID NOs: 13 and 14;

consist of SEQ ID NOs: 20 and 21;

consist of SEQ ID NOs: 22 and 23;

consist of SEQ ID NOs: 25 and 26;

consist of SEQ ID NOs: 28 and 29; or comprise SEQ ID NO: 28 and comprise a nucleic acid sequence at least 95% identical to SEQ ID NO: 29; and wherein each oligonucleotide in the oligonucleotide primer pair is operably linked to a detectable label, and wherein the detectable label comprises a radioactive isotope, a chemiluminescent or fluorescent agent, a hapten, or an enzyme; and instructions for diagnosing a chordopoxvirus infection in a subject.

* * * * *

SEQUENCE LISTING

<160> NUMBER OF SEQ ID NOS: 30

<210> SEQ ID NO 1
<211> LENGTH: 230
<212> TYPE: DNA
<213> ORGANISM: Variola virus

<400> SEQUENCE: 1

```
acaccaaaaa ctcatataac ttctagatgt agaagcatta gctaaaaaaa tagtagaatc      60
aaaggatata agtagatgtt ccaacaagtg agcaattccc aaaatttcat ctatatcatt     120
ctcaaatccg aaattagaaa ttcccaagta gatatctttt tcatccgat cattaataaa     180 aatacgaact ttattcggta agacgatcat ttactaagga gtaaaatagg                230
```

<210> SEQ ID NO 2
<211> LENGTH: 230
<212> TYPE: DNA
<213> ORGANISM: Monkeypox virus

<400> SEQUENCE: 2

```
acaccaaaaa ctcatataac ttctagatgt agaagcattc gctaaaaaat tagtagaatc      60
aaaggatata agtagatgtt ccaacaagtg agcaattccc aagatttcat ctatatcatt     120
ctcgaatccg aaattagaaa ttcccaagta gatatccttt tcatccgat cattgatgaa     180 aatacgaact ttattcggta agacgatcat ttactaagga gtaaaatagg                230
```

<210> SEQ ID NO 3
<211> LENGTH: 230
<212> TYPE: DNA
<213> ORGANISM: Cowpox virus

<400> SEQUENCE: 3

```
acaccaaaaa ctcatataac ttctagatgt agaagcatta gctaaaaaat tagtagaatc      60
aaaggatata agtagatgtt ccaacaagtg agcaattccc aagatttcat ctatatcatt     120
ctcgaatccg aaattagaaa ttcccaagta gatatccttt tcatccgat cattgatgaa     180 aatacgaact ttattcggta agacgatcat ttactaagga gtaaaatagg                230
```

<210> SEQ ID NO 4
<211> LENGTH: 230
<212> TYPE: DNA
<213> ORGANISM: Vaccinia virus

<400> SEQUENCE: 4

```
acaccaaaaa ctcatataac ttctagatgt agaagcattc gctaaaaaat tagtagaatc      60
aaaggatata agtagatgtt ccaacaagtg agcaattccc aagatttcat ctatatcatt     120
ctcgaatccg aaattagaaa ttcccaagta gatatccttt tcatccgat cattgatgaa     180 aatacgaact ttattcggta agacaatcat ttactaagga gtaaaatagg                230
```

<210> SEQ ID NO 5
<211> LENGTH: 230
<212> TYPE: DNA
<213> ORGANISM: Swinepox virus

<400> SEQUENCE: 5

```
acaccaaaaa ctcatgtaac ttctagcagt ggatgcgttt gctataaatt tagatgaatc      60
aaaatctata agtatatgtt ctaatagatg agcaattcct agaacttcat atatatcatt     120
ttcaaatcca aatctggata ttcccaaata aatatcctta tgcatagagt tatctataaa     180
```

```
tatcctaaca ccgttggata atactatcat ttactaagga gtaaaatagg        230
```

<210> SEQ ID NO 6
<211> LENGTH: 230
<212> TYPE: DNA
<213> ORGANISM: Deerpox virus

<400> SEQUENCE: 6

```
acaccaaaaa ctcatataac ttcttgcagt tgatgcattt gcaacatatt tcgatgaatc    60
aaacgatatt aaaatgtgtt ctaacaaatg tgcaacgccc aatatgtttc ctatatcatt   120
ttcaaagcca aagctagcaa ttcctaaata aatatctttt atcatatacg gatttataaa   180
aattctaaca ccatttgata gcactatcat ttactaagga gtaaaatagg              230
```

<210> SEQ ID NO 7
<211> LENGTH: 230
<212> TYPE: DNA
<213> ORGANISM: Myxoma virus

<400> SEQUENCE: 7

```
acaccaaaaa ctcatataac ttctggccgt ggaggcattt gcgacgaacc gggacgcgtc    60
gaacgagatg agtatatgct ctaatagatg cgctatgccc agtataccct ctatgtcttt   120
ttcgaatcca aacccggaaa accctacgta gatatctttg ttcgtggaag aattaataaa   180
cacgcgtgtc ccgttatcga agacgatcat ttactaagga gtaaaatagg              230
```

<210> SEQ ID NO 8
<211> LENGTH: 230
<212> TYPE: DNA
<213> ORGANISM: Rabbit fibroma virus

<400> SEQUENCE: 8

```
gcaccaaaaa ctcatataac ttctagccgt ggaggcattt gcgatgaacc gggacacatc    60
gaacgagata agtatatgtt ccaacagatg tgccgtaccc agtataccct ctatgtcctt   120
ttcgaatccg aacccagaaa tccctacgta tatatctttg ttcgtggaag tgtttataaa   180
tacacgcacc ccgttatcga atacaatcat ttactaagga gtaaaatagg              230
```

<210> SEQ ID NO 9
<211> LENGTH: 230
<212> TYPE: DNA
<213> ORGANISM: sheeppox virus

<400> SEQUENCE: 9

```
acaccaaaaa ctcatatagc ttcttgcagt ggaagcgttt gcaacaaatt ttgatggatc    60
aaaagtgata agaatatgtt ctaacaaatg tgctatacct attatattac caatatcatt   120
ttcaaaccca aaactagcaa ttcctaaata tatatctttg ttcatgagtt catcaataaa   180
tattctaact ccatttgaaa gaactatcat ttactaagga gtaaaatagg              230
```

<210> SEQ ID NO 10
<211> LENGTH: 230
<212> TYPE: DNA
<213> ORGANISM: lumpy skin disease virus

<400> SEQUENCE: 10

```
acaccaaaaa ctcatatagc ttcttgcagt ggaagcgttt gcgacaaatt ttgatggatc    60
aaaagtgata agaatatgtt ctaacaaatg tgctatacct attatattac caatatcatt   120
```

```
ttcaaaccca aaactagcaa ttcctaaata tatatctttg ttcatgagtt catcaataaa      180
tattctaact ccatttgaaa gaactatcat ttactaagga gtaaaatagg                230
```

<210> SEQ ID NO 11
<211> LENGTH: 230
<212> TYPE: DNA
<213> ORGANISM: Yaba monkey tumor virus

<400> SEQUENCE: 11

```
acaccaaaaa ctcatatatt ttctagccgt tgatgcgttt gctataaact agaagaatc       60 aaatgaaatt aatatatgtt ccagcaaatg agccactcct aatatttcac ctatgtcatt     120
ttcaaaccca aaactcgcaa cgcctaagta tatatcttta ttcatatcat catttatgaa     180
tatcctaaca ccgtttgaca aaactatcat ttactaagga gtaaaatagg                230
```

<210> SEQ ID NO 12
<211> LENGTH: 230
<212> TYPE: DNA
<213> ORGANISM: Tanapox virus

<400> SEQUENCE: 12

```
acaccaaaaa ctcatatatt ttcttgcagt tgacgcgttt gcaacaaact tggatgagtc      60
aaaggaaatt aaaatatgtt caagcaaatg agctattcct aatatttcac ctatatcgtt    120
ttcaaatcca aaactagcaa ttcctaggta aatatcttta ttcatattac tattaatgaa    180
tattctaaca ccgttagata aaactatcat ttactaagga gtaaaatagg                230
```

<210> SEQ ID NO 13
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 13

```
acaccaaaaa ctcatataac ttct                                            24
```

<210> SEQ ID NO 14
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 14

```
cctattttac tccttagtaa atgat                                           25
```

<210> SEQ ID NO 15
<211> LENGTH: 627
<212> TYPE: DNA
<213> ORGANISM: Bovine papular stomatitis virus

<400> SEQUENCE: 15

```
catccccaag gagaccaacg agctcacgta cctgctgggc atgatcgtga agtactgctc      60
catgaacgcc gaggagcagg tgatccagcg cgcgatgatc gagtacgaca acatcaagat    120
catctcgtcg aactccagca gcatcaacct ctcgtacatc atctccggca agagcaacat    180
gctgcgcagc ttcgtggtgg cgcgccgcaa ggaccagacc gcgcgttccg tcatcgggcc    240
ggattcgtcg ctctcggtgc gcgaggtcgg catccccgac tacatccgca acacgctcac    300
gcagaaggtc ttcgtcaact acctgacgtc caagcgcgtg cgcgcgctct tcgaggagcg    360
```
ctccgtgaag ttctacttca acaagcgcct gcgtcagctc acgcgcatca aggacgggaa 420
gttcatcaaa gacaagatcc acctgctgcc cggagactgg gtggagatcg ccatgaccga 480
gggcacgaac gtgatcttcg gccggcagcc ctcgctgcac cgacacaacg tcatctcgtc 540
caccgcgcgc gcctcgctcg ggtacacgat caagatcccg ccggggatcg ccaactcgca 600
gaacgccgac ttcgacggcg acgagga 627

<210> SEQ ID NO 16
<211> LENGTH: 627
<212> TYPE: DNA
<213> ORGANISM: Orf virus

<400> SEQUENCE: 16
tcctcgtcgc cgtcgaagtc cgcgttctgc gagttcgcga tcccgggcgg gatcttgatg 60
gtgtagccgg gcgaggcgcg cgcggtcgag gatatgacgt tgtgtcggtg cagcgagggc 120
tggcggccga atatcacgtt cgtgccctcg gacatgggga tctccaccca gtcgccgggc 180
agcaggtgga tcttgtcctt gatgaacttg ccctccttga tgcgcgtgag ctggcgcagc 240
cgcttgttga agtagaactt gaccgcgcgg tcctcgaaca gcgcgcgcac gcgcttgctg 300
gtgaggtagt tcacgaacac cttctgcgtg agcgtgttcc ggatgtagtc ggggatgccg 360
acctcgcaca ccgagagcgc ggagtcgggc ccgatgaccg agcgcgcggt ctggtccttg 420
cgccgcgcga ccacgaagct gcgcagcatg ttgctcttgc ccgcgatgat gtaggagagg 480
ttgatgctgc tcgagttcga ggagatgatc ttgatgttgt cgtactcgat cacggcgcgc 540
tggatgacct gctcctcggc gttcatggag cagtacttca cgatcatgcc cagcaggtag 600
gtgagctcgt tggtctcctt ggggatg 627

<210> SEQ ID NO 17
<211> LENGTH: 627
<212> TYPE: DNA
<213> ORGANISM: Orf virus

<400> SEQUENCE: 17
tcctcgtcgc cgtcgaagtc cgcgttctgc gagttcgcga tcccgggcgg gatcttgatg 60
gtgtagccgg gcgaggcgcg tgcggtcgag gatatgacgt tgtgtcggtg cagcgagggc 120
tggcggccga atatcacgtt cgtgccctcg gacatgggga tctccaccca gtcgccgggc 180
agcaggtgga tcttgtcctt gatgaacttg ccctccttga tgcgcgtgag ctggcgcagc 240
cgcttgttga agtagaactt gaccgcgcgg tcctcgaaca gcgcgcgcac gcgcttgctg 300
gtgaggtagt tcacgaacac cttctgcgtg agcgtgttcc ggatgtagtc ggggatgccg 360
acctcgcaca ccgagagcgc ggagtcgggc ccgatgaccg agcgcgcggt ctggtccttg 420
cgccgcgcta ccacgaagct gcgcagcatg ttgctcttgc ccgcgatgat gtaggagagg 480
ttgatgctgc tagagttaga ggagatgatc ttgatgttgt cgtactcgat cacggcgcgc 540
tggatgacct gctcctcggc gttcatggag cagtacttca cgatcatgcc cagcaggtag 600
gtgagctcgt tggtctcctt ggggatg 627

<210> SEQ ID NO 18
<211> LENGTH: 627
<212> TYPE: DNA
<213> ORGANISM: Crocodilepox virus

<400> SEQUENCE: 18

```
tcctcgtcgc cgtcgaagtc cgcgttctgc gagttcgcga tgccgggcga gatcttgatc      60
gtgttctcgg ccgtcgcgcg gatcgacgac gagatgacgt tgtagcggtg cagcgacggc     120
tgccgcccga agatgatgtt ggagaactcc tgcaggtcga tctccaccca gtcgcccggc     180
agcaggtgga tcttgttctt gatgaacttg ttcttcttca ggctcgtcag ctgccgcagg     240
ctcttgttga agtagaactt gattttgttg gccttgaaca gctcgcgcac gcggtcgatg     300
gtgaaggcgt tcacgaagat cttctcggtc agcgtcggc gcacgtagtc ggggatgccc     360
acctccgcca cgctcagcga cgagtcgggg cccagcacgg accgcgccgt ctgatctttg     420
cgccgcgcca cgatgtagct gcggatcatg ttgttttgc cggaggtgat gtacgacagg     480
ttgatgttcg aggtgttggt cacgaggatc ttgttgttgt cgtactcgat gaccgccttc     540
tggatggtgt actcctccgc gttctggatg cagtacttca cgatcgtgtt cagcatgtac     600
gtgatctcgt tggtctcctt ggggatg                                         627

<210> SEQ ID NO 19
<211> LENGTH: 630
<212> TYPE: DNA
<213> ORGANISM: Molluscum contagiosum virus

<400> SEQUENCE: 19
tcctcgtcgc cgtcgaagtc cgcgttctgc gagttggcaa tgccgggcgg gatcttgatc      60
gtgtccccgc tcgtggcgcg cacggacgag gagattacgt tgtacttgtg cagcgaaggc     120
tggcgcccga agatgatgct ggtgaactcg cgcacgcgcg tctccaccca gtccccgggc     180
agcaggtgga ttttgttctt gacaaacttg ttgggcttga tgcgagtgag ctggcccagc     240
cgcttgttga agtagaactt gacctcgttc ctgcggaaga gctcctccac ggcgggcacc     300
gtgaaggcgt tcacgaagac cttctcggtg agcgtgttgc gcacgtagtc ggggatgccc     360
acctcggtaa ttgacagctc ggggtcgggg cccagcacgg agcgcgccgt ctggtctttg     420
cggcgcgcca ccatgtaact gcggatcatg ttgttcttgc cagacgtaat gtaggacagg     480
ttgatactgg aggtgttatt gttcacgatg atcttgatgt tgtcgtactc gatgaccgcc     540
ttctgcaaca cctgctcctc ggcgttcatg ttgctgtact tcacgatcat gcccagcagg     600
taggtgagct cgttggtctc cttggggatg                                      630

<210> SEQ ID NO 20
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 20
catccccaag gagaccaacg ag                                               22

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
tcctcgtcgc cgtcgaagtc                                                  20

<210> SEQ ID NO 22
<211> LENGTH: 23
```

```
<212> TYPE: DNA
<213> ORGANISM: Artificial sequence
<220> FEATURE:
<223> OTHER INFORMATION: Synthetic oligonucleotide

<400> SEQUENCE: 22
acaccaaaaa ctcatataag tgc                                           23

<210> SEQ ID NO 23
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 23
ttatttttac cattaattaa atgat                                         25

<210> SEQ ID NO 24
<211> LENGTH: 233
<212> TYPE: DNA
<213> ORGANISM: Canarypox virus

<400> SEQUENCE: 24
acaccaaaaa ctcatataag tgcgtgatgt actagcgttg gcattaaagt acttattatc   60
gaatgatatg agtatatgtt ccaataaatg agctatacca agaacatcat catgtatatc  120
tttttcaaaa ccaaagtcag aaatacctat ataaatatct tttcgcatag aatggttaac  180
aaatatacga acaccatttt ttaatagaat catttaatta atggtaaaaa taa         233

<210> SEQ ID NO 25
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 25
acaccagaaa ctcatatacg tac                                           23

<210> SEQ ID NO 26
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 26 cttatttaa ctgtacttaa atgat                                          25

<210> SEQ ID NO 27
<211> LENGTH: 233
<212> TYPE: DNA
<213> ORGANISM: Fowlpox virus

<400> SEQUENCE: 27
acaccaaaaa ctcatataag tgcgtgatgt actagcgttg gcattaaagt acttattatc   60
gaatgatatg agtatatgtt ccaataaatg agctatacca agaacatcat catgtatatc  120
tttttcaaaa ccaaagtcag aaatacctat ataaatatct tttcgcatag aatggttaac  180
aaatatacga acaccatttt ttaatagaat catttaatta atggtaaaaa taa         233

<210> SEQ ID NO 28
```

```
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 28
cattccaaaa gaaacaaacg aactt                                        25

<210> SEQ ID NO 29
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 29
tcttcgtctc cgtcaaagtc agc                                          23

<210> SEQ ID NO 30
<211> LENGTH: 627
<212> TYPE: DNA
<213> ORGANISM: Sealpox virus

<400> SEQUENCE: 30
cattccaaaa gaaacaaacg aacttacgta cttgctaggg atgattgtaa agtactgctc    60
tatgaacgct gaagagcagg ttattcagcg cgcagtaatt gagtacgaca acatcaagat   120
aatctcgtct aactcaaaca gcattaacct atcgtacatc atcgcaggca agagcaacat   180
gctgcgcagc tttgtagtag cgcggcgcaa agaccaaact gcgcgctcag ttattgggcc   240
tgactctgct ctctcggtgt gcgaagtggg cattccagac tacattcgca acacgctaac   300
gcaaaaaatc ttcgtaaact acctaacttc gcagcgcgtg cgcgcactgt ttgaggagcg   360
cgcagttaag ttttacttta acaagcggct gcgccagctc acgcgcatca aagacgggaa   420
gtttatcaaa gacaaaattc acctgctgcc tggcgactgg gtggaggtgc ccatgtctga   480
aggcacaaac gtgatatttg ggcgccagcc ctcgctgcac cgacacaacg ttatctcttc   540
aactgcgcgg ccgtcacccg gacacaccat caaaattccg ccgggaattg caaactcgca   600
aaacgctgac tttgacggag acgaaga                                      627
```